United States Patent

Reiser et al.

Patent Number: 4,486,218
Date of Patent: Dec. 4, 1984

[54] 1-VINYLTRIAZOLE COMPOUNDS AND PLANT GROWTH AND FUNGICIDAL COMPOSITIONS

[75] Inventors: Wolf Reiser; Wilfried Draber; Karl H. Büchel, all of Wuppertal; Klaus Lürssen, Bergisch-Gladbach; Paul-Ernst Frohberger, Leverkusen; Volker Paul, Solingen, all of Fed. Rep. of Germany

[73] Assignee: Bayer Aktiengesellschaft, Leverkusen, Fed. Rep. of Germany

[21] Appl. No.: 294,603

[22] Filed: Aug. 20, 1981

Related U.S. Application Data

[63] Continuation of Ser. No. 112,891, Jan. 17, 1980, abandoned.

[51] Int. Cl.³ ............... A01N 43/64; C07D 249/08
[52] U.S. Cl. ........................... 71/76; 71/77; 71/78; 71/92; 424/232; 424/245; 424/269; 548/101; 548/262; 568/420; 568/425; 568/445; 568/446; 568/448
[58] Field of Search ............ 542/429; 548/101, 262; 424/245, 232, 269; 71/92, 76, 77, 78

[56] References Cited

U.S. PATENT DOCUMENTS

| | | | |
|---|---|---|---|
| 4,086,351 | 4/1978 | Balasubramanyan et al. | 548/266 |
| 4,182,862 | 1/1980 | Chan | 548/341 |
| 4,203,995 | 5/1980 | Funaki et al. | 424/269 |
| 4,243,405 | 1/1981 | Balasubramanyan et al. | 424/269 |

FOREIGN PATENT DOCUMENTS

| | | | |
|---|---|---|---|
| 2645617 | 4/1977 | Fed. Rep. of Germany | |
| 1464224 | 2/1977 | United Kingdom | 548/262 |

Primary Examiner—Alton D. Rollins
Attorney, Agent, or Firm—Felfe & Lynch

[57] ABSTRACT

1-Vinyltriazole compounds of the formula

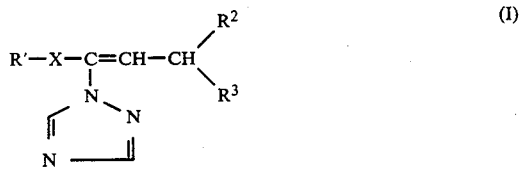

wherein
R¹ is alkyl, substituted alkyl, cycloalkyl, aryl or substituted aryl;
R² is alkyl;
R³ is alkyl, cycloalkyl, cycloalkenyl, substituted cycloalkenyl, alkenyl, aryl or substituted aryl; or
R² and R³, together with the carbon to which they are bonded, represent cycloalkenyl, substituted cycloalkenyl, cycloalkyl or substituted cycloalkyl;
X is the group

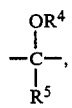

or, alternatively,
X may represent a keto group provided that when X is a keto group, R¹ is alkyl, substituted alkyl, cycloalkyl, or substituted cycloalkyl;
R⁴ is hydrogen, alkyl, aralkyl, substituted aralkyl, acyl, carbamoyl or substituted carbamoyl;
R⁵ is hydrogen, alkyl, aralkyl or substituted aralkyl;
and acid addition salts and metal salt complexes thereof; are outstandingly effective plant growth regulants and as fungicides.

36 Claims, No Drawings

1-VINYLTRIAZOLE COMPOUNDS AND PLANT GROWTH AND FUNGICIDAL COMPOSITIONS

This is a continuation of Ser. No. 112,891 filed Jan. 17, 1980, abandoned.

This invention relates to certain 1-vinyltriazole compounds, to plant growth regulant compositions and fungicidal compositions containing them, and to methods for regulating plant growth and for combating fungi.

It is known that certain 2-haloethyl-trialkylammonium halides have plant growth regulating properties (see U.S. Pat. No. 3,156,554). Thus, for example, an influencing of plant growth, in particular an inhibition of vegetative plant growth, can be achieved in important crop plants with the aid of 2-chloroethyltrimethylammonium chloride. However, the activity of this substance is not always adequate, especially when small amounts are used.

It is also known that 2-chloroethylphosphonic acid has a plant growth regulating action (see DE-OS (German Published Specification) No. 1,667,968). However, the results achieved with this substance are likewise not always satisfactory.

Furthermore, it is known that acylated and carbamoylated derivatives of 3,3-dimethyl-1-phenoxy-1-triazolyl-butan-2-ols, which are substituted in the phenyl part, have a good fungicidal activity (see DE-OS (German Published Specification) No. 2,600,799). Certain 4,4-dimethyl-1-phenyl-2-triazolyl-pentan-3-ones, which are substituted in the phenyl part, for example, 1-(4-chlorophenyl)-4,4-dimethyl-2-(1,2,4-triazol-1-yl)-pentan-3-one, are likewise suitable for combating fungi (see DE-OS (German Published Specification) No. 2,734,426). However, the action of these azole derivatives is not always completely satisfactory, especially when small amounts and low concentrations are used.

The present invention now provides, as new compounds, the 1-vinyl-triazole derivatives of the formula $$R'-X-\underset{\underset{N}{\overset{N}{\underset{\|}{\overset{}{|}}}}\underset{N}{\overset{}{\diagdown}}}{C}=CH-CH\diagup_{R^3}^{R^2} \quad (I)$$

in which
R$^1$ represents optionally substituted alkyl, cycloalkyl or optionally substituted aryl,
R$^2$ represents alkyl and
R$^3$ represents alkyl, cycloalkyl, optionally substituted cycloalkenyl, alkenyl or optionally substituted aryl, or
R$^2$ and R$^3$, together with the carbon atom to which they are bonded, represent optionally substituted cycloalkenyl or cycloalkyl,
X represents the group $$-\underset{R^5}{\overset{OR^4}{\underset{|}{\overset{|}{C}}}}-,$$

or alternatively may represent the keto group provided that R$^1$ represents optionally substituted alkyl or cycloalkyl,
R$^4$ represents hydrogen, alkyl, optionally substituted aralkyl, acyl or optionally substituted carbamoyl, and
R$^5$ represents hydrogen, alkyl or optionally substituted aralkyl,
and acid addition salts and metal salt complexes thereof.

It has been found that the 1-vinyltriazole derivatives of the formula (I) and acid addition salts and metal salt complexes thereof have powerful plant growth regulating properties and powerful fungicidal properties.

Preferably, in formula (I),
R$^1$ represents straight-chain or branched alkyl with 1 to 4 carbon atoms [which optionally carries one or two substituents selected independently from, preferably, halogen, alkylcarbonyloxy with 1 to 4 carbon atoms in the alkyl part, alkylsulphonyloxy with 1 to 4 carbon atoms and phenylsulphonyloxy which is itself optionally substituted by halogen or by alkyl with 1 to 4 carbon atoms], cycloalkyl with 5 to 7 carbon atoms or aryl with 6 to 10 carbon atoms (such as phenyl or naphthyl) [which aryl optionally carries one or more substituents selected independently from, preferably, halogen, alkyl with 1 to 4 carbon atoms, phenyl, phenoxy, halophenyl and halophenoxy],
R$^2$ represents straight-chain or branched alkyl with 1 to 4 carbon atoms, and
R$^3$ represents straight-chain or branched alkyl with 1 to 4 carbon atoms, cycloalkyl with 5 to 7 carbon atoms, cycloalkenyl with 5 to 7 carbon atoms [which is optionally substituted by alkyl with 1 to 4 carbon atoms], alkenyl with 2 to 4 carbon atoms or aryl with 6 to 10 carbon atoms (such as phenyl or naphthyl) [which is optionally substituted by, preferably, halogen or alkyl with 1 to 4 carbon atoms], or
R$^2$ and R$^3$, together with the carbon atom to which they are bonded, represent cycloalkenyl with 5 to 7 carbon atoms [which is optionally substituted by alkyl with 1 to 4 carbon atoms] or cycloalkyl with 3 to 7 carbon atoms,
X represents the group —C(OR$^4$)R$^5$—, or may represent the keto group provided R$^1$ represents optionally substituted alkyl or cycloalkyl,
R$^4$ represents hydrogen, straight-chain or branched alkyl with 1 to 4 carbon atoms, aralkyl with 1 to 2 carbon atoms in the alkyl part and 6 to 10 carbon atoms in the aryl part (such as benzyl or naphthylmethyl) [which optionally carries one or more substituents selected independently from, preferably, halogen, alkyl with 1 to 4 carbon atoms, haloalkyl with up to 2 carbon atoms and up to 3 identical or different halogen atoms (preferred halogen atoms being fluorine and chlorine) and phenyl and phenoxy, the last two being themselves optionally substituted by halogen], the acyl radical —CO—R$^{10}$ or the carbamoyl radical —CO—NR$^{11}$R$^{12}$,
R$^5$ represents hydrogen, alkyl with 1 to 4 carbon atoms or aralkyl with 1 to 2 carbon atoms in the alkyl part and 6 to 10 carbon atoms in the aryl part (such as benzyl) [which is optionally substituted by halogen or alkyl with 1 to 4 carbon atoms],
R$^{10}$ represents straight-chain or branched alkyl with 1 to 4 carbon atoms, haloalkyl with 1 to 2 carbon atoms and 1 to 5 identical or different halogen atoms (preferably fluorine and chlorine atoms) or phenyl or benzyl [either of which is optionally substituted by, preferably, halogen or alkyl with 1 to 4 carbon atoms], $R^{11}$ represents hydrogen or alkyl with 1 to 4 carbon atoms, and $R^{12}$ represents alkyl with 1 to 8 carbon atoms, haloalkyl with up to 4 carbon atoms and up to 5 identical or different halogen atoms (especially fluorine or chlorine atoms), aryl with 6 to 10 carbon atoms (such as phenyl or naphthyl) [which optionally carries one or more substituents selected independently from, preferably, halogen, alkyl with 1 to 4 carbon atoms and haloalkyl with up to 2 carbon atoms and up to 5 identical or different halogen atoms (especially fluorine and chlorine atoms)] or haloalkylmercapto with 1 to 2 carbon atoms and up to 5 halogen atoms (especially fluorine and chlorine atoms).

The compounds of the formula (I) can exist in two geometric isomer forms, depending on the arrangement of the groups which are bonded to the double bond. If X represents the group $-C(OR^4)R^5-$, an asymmetric carbon atom is present, so that in this case the compounds of the formula (I) are also obtained in two optical isomer forms. The formula (I) therefore embraces both the individual isomers and the isomer mixtures.

The invention also provides a process for the preparation of a 1-vinyltriazole derivative of the formula (I), or an acid addition salt or metal salt complex thereof, in which (a) a triazole-ketone of the general formula

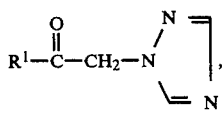  (II)

in which $R^1$ has the meaning indicated above,
is reacted with an aldehyde of the general formula

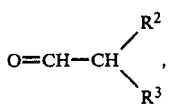  (III)

in which $R^2$ and $R^3$ have the meanings indicated above, in the presence of a solvent and in the presence of a catalyst, and from the isomers which form, as a result of splitting off of water, the desired isomeric product of the general formula

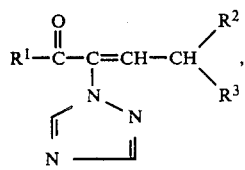  (Ia)

in which $R^1$, $R^2$ and $R^3$ have the meanings indicated above,
is isolated by customary methods, or (b) a compound, obtainable by process variant (a), of the general formula

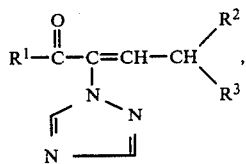  (Ia)

in which $R^1$, $R^2$ and $R^3$ have the meanings indicated above
is either (α) reduced with a complex hydride in the presence of a solvent, or (β) reduced with a Grignard compound of the general formula

  (IV), in which
$R^6$ represents alkyl or optionally substituted aralkyl and
Hal represents halogen,
in the presence of a solvent, or (c) a compound, obtainable by process variant (b)(α) or (b)(β), of the general formula

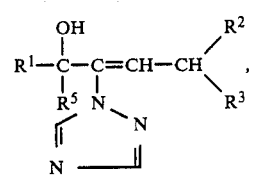  (Ib)

in which $R^1$, $R^2$, $R^3$ and $R^5$ have the meanings indicated above, is reacted with a halide of the general formula

  (V), in which
$R^7$ represents alkyl, optionally substituted aralkyl, acyl or optionally substituted carbamoyl and
Hal' represents halogen,
in the presence of a solvent, and if appropriate in the presence of a strong base or if appropriate in the presence of an acid-binding agent, or (d) a compound, obtainable by process variant (b)(α) or (b)(β), of the general formula

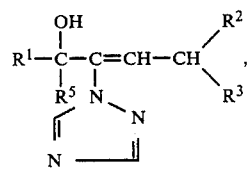  (Ib)

in which $R^1$, $R^2$, $R^3$ and $R^5$ have the meanings indicated above,
is reacted with an acid anhydride of the general formula

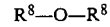  (VI), in which $R^8$ represents acyl,
in the presence of a solvent and if appropriate in the presence of a catalyst, or (e) a compound obtainable by process variant (b)(α) or (b)(β), of the general formula

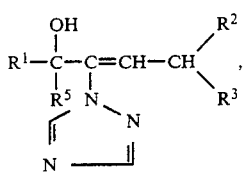
(Ib)

is reacted with an isocyanate of the general formula $$O=C=N-R^9 \quad (VII),$$

in which $R^9$ represents alkyl, haloalkyl or optionally substituted aryl,
in the presence of a solvent and if appropriate in the presence of a catalyst, and, if required, an acid or a metal salt is then added onto the compound obtained by any of process variants (a) to (e).

Surprisingly, the 1-vinyltriazoles according to the invention and acid addition salts and metal salt complexes thereof exhibit a better plant growth regulating action than the known 2-chloroethyl-trimethylammonium chloride and 2-chloroethylphosphonic acid, which is likewise known, which are recognized as substances of the same type of action which have a good activity. Surprisingly, the compounds according to the invention also have a better fungicidal action than the acylated and carbamoylated derivatives of 3,3-dimethyl-1-phenoxy-1-triazolyl-butan-2-ols substituted in the phenyl part, which are known from the state of the art, and than 1-(4-chlorophenyl)-4,4-dimethyl-2-(1,2,4-triazol-1-yl)-pentan-3-one, which is likewise known, which are closely related compounds chemically and from the point of view of their action. The active compounds according to the invention thus represent an enrichment of the art.

Those compounds of the formula (I) are especially preferred in which $R^1$ represents tert.-butyl, isopropyl, chloro-tert.-butyl, bromo-tert.-butyl, fluoro-tert.-butyl, acetoxy-tert.-butyl, methylsulphonyloxy-tert.-butyl, p-toluenesulphonyloxy-tert.-butyl, 1,3-dichloro-2-methyl-prop-2-yl, 1,3-dibromo-2-methyl-prop-2-yl, 1,3-difluoro-2-methyl-prop-2-yl, 1-chloro-3-bromo-2-methyl-prop-2-yl, 1,3-diacetoxy-2-methyl-prop-2-yl, cyclohexyl, phenyl, chlorophenyl, bromophenyl, dichlorophenyl, fluorophenyl, methylphenyl, dimethylphenyl, chloro-methylphenyl, biphenylyl, phenoxyphenyl, chlorophenylphenyl or chlorophenoxyphenyl; $R^2$ represents methyl, ethyl, propyl or butyl and $R^3$ represents methyl, ethyl, isopropyl, cyclohexyl, cyclohexenyl, methylcyclohexenyl, allyl, methacryl, phenyl, chlorophenyl, dichlorophenyl or methylphenyl; or $R^2$ and $R^3$, together with the carbon atom to which they are bonded, represent cyclopropyl, cyclobutyl, cyclopentyl, cyclohexyl, cyclohexenyl or methylcyclohexenyl; X represents the group $-C(OR^4)R^5$, or alternatively the keto group, provided $R^1$ has the optionally substituted alkyl or cycloalkyl meanings indicated; $R^4$ represents hydrogen, methyl, ethyl, n-propyl, isopropyl, isobutyl, naphthyl which is optionally substituted by chlorine, benzyl which is optionally monosubstituted or polysubstituted by identical or different substituents from the group consisting of chlorine, fluorine, methyl, phenyl, chlorophenyl, phenoxy and chlorophenoxy, the acyl radical $-CO-R^{10}$ or the carbamoyl radical $-CO-NR^{11}R^{12}$; $R^5$ represents hydrogen, methyl, ethyl, isopropyl, benzyl, chlorobenzyl or dichlorobenzyl; $R^{10}$ represents methyl, ethyl, isopropyl, isobutyl, chloromethyl, dichloromethyl or phenyl or benzyl, either of which is optionally monosubstituted or polysubstituted, the substituents being chlorine, bromine or methyl; $R^{11}$ represents hydrogen, methyl or ethyl; and $R^{12}$ represents methyl, ethyl, chloroethyl, phenyl, chlorophenyl, trifluoromethyl, chlorodifluoro-methyl, dichloro-fluoromethyl or trichloromethyl-mercapto.

The following compounds of the general formula (I) may be mentioned specifically, in addition to the compounds mentioned later in the preparative examples:

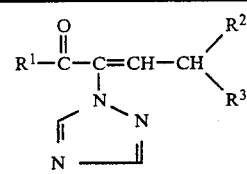
(Ia)

| $R^1$ | $R^2$ | $R^3$ |
|---|---|---|
| C(CH$_3$)$_3$ | C$_2$H$_5$ | C$_2$H$_5$ |
| C(CH$_3$)$_3$ | C$_2$H$_5$ | CH$_3$ |
| C(CH$_3$)$_3$ | CH$_3$ | CH$_3$ |
| C(CH$_3$)$_3$ | CH$_3$ | ⬡H |
| C(CH$_3$)$_3$ | CH$_3$ | ⬡ |
| C(CH$_3$)$_3$ | | Cyclopropyl |
| C(CH$_3$)$_3$ | | Cyclobutyl |
| C(CH$_3$)$_3$ | | Cyclopentyl |
| C(CH$_3$)$_3$ | | Cycloheptyl |
| C(CH$_3$)$_3$ | | Norbon-3-en-2-yl |
| ClCH$_2$-C(CH$_3$)$_2$- | | Cyclohexane |
| ClCH$_2$-C(CH$_3$)$_2$- | | Cyclohexane |
| ClCH$_2$-C(CH$_3$)$_2$- | | Methylcyclohexene |
| ClCH$_2$-C(CH$_3$)$_2$- | CH$_3$ | CH$_3$ |
| BrCH$_2$-C(CH$_3$)$_2$- | | Cyclohexane |
| BrCH$_2$-C(CH$_3$)$_2$- | | Cyclohexene |
| BrCH$_2$-C(CH$_3$)$_2$- | | Methylcyclohexene |

-continued

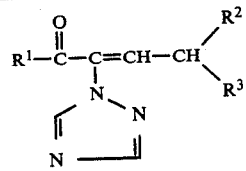
(Ia)

| $R^1$ | $R^2$ | $R^3$ |
|---|---|---|
| 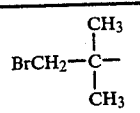 | Methylcyclohexene | |
| 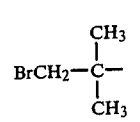 | CH$_3$ | CH$_3$ |
| 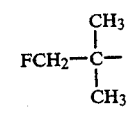 | Cyclohexane | |
| 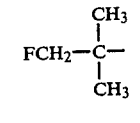 | Cyclohexene | |
| 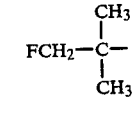 | Methylcyclohexene | |
| 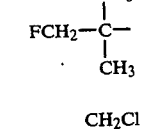 | CH$_3$ | CH$_3$ |
| 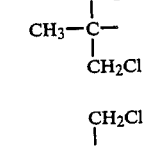 | Cyclohexane | |
| 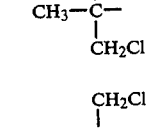 | Cyclohexene | |
| 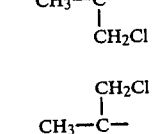 | Methylcyclohexene | |
| 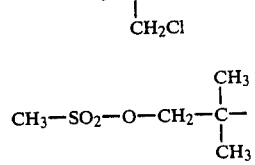 | CH$_3$ | CH$_3$ |
| 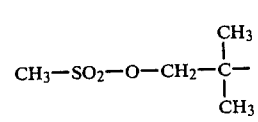 | Cyclohexane | |
| 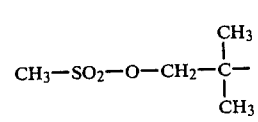 | Cyclohexene | |

-continued

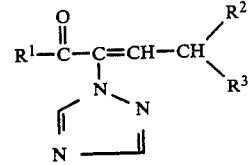
(Ia)

| $R^1$ | $R^2$ | $R^3$ |
|---|---|---|
| 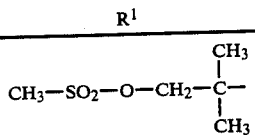 | Methylcyclohexene | |
| 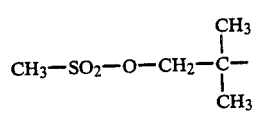 | CH$_3$ | CH$_3$ |
| 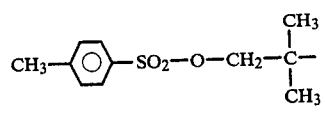 | Cyclohexane | |
| 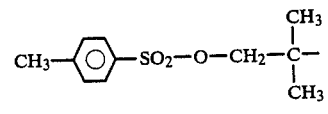 | Cyclohexene | |
| 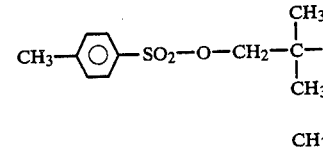 | Methylcyclohexene | |
| 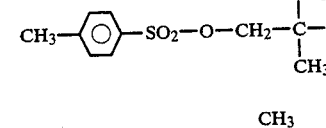 | CH$_3$ | CH$_3$ |
| 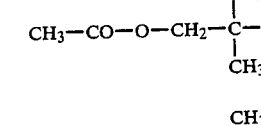 | Cyclohexane | |
| 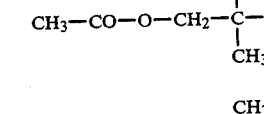 | Cyclohexene | |
| 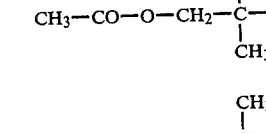 | Methylcyclohexene | |
| 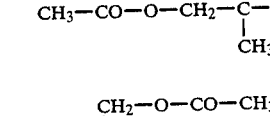 | CH$_3$ | CH$_3$ |
| 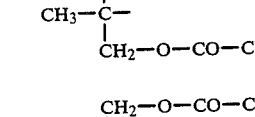 | Cyclohexane | |
| 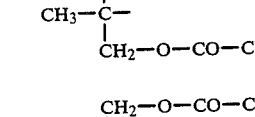 | Cyclohexene | |

TABLE-continued (Ia)

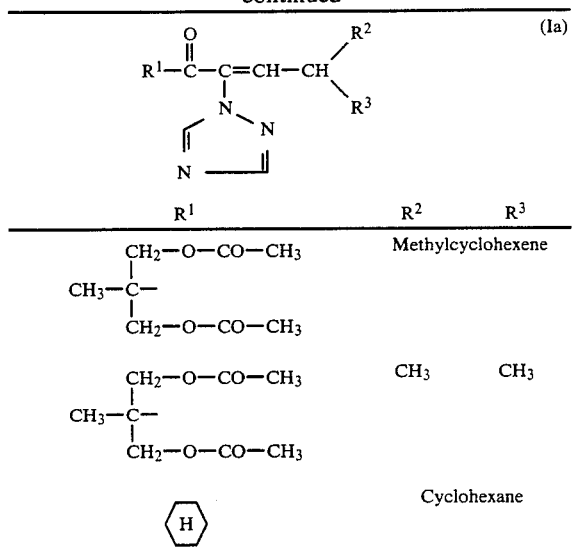

| R¹ | R² | R³ |
|---|---|---|
| CH₃-C(CH₂-O-CO-CH₃)₂-CH₃ (neopentyl diacetate structure) | | Methylcyclohexene |
| CH₃-C(CH₂-O-CO-CH₃)₂-CH₃ | CH₃ | CH₃ |
| phenyl (H) | | Cyclohexane |

TABLE-continued (Ia)

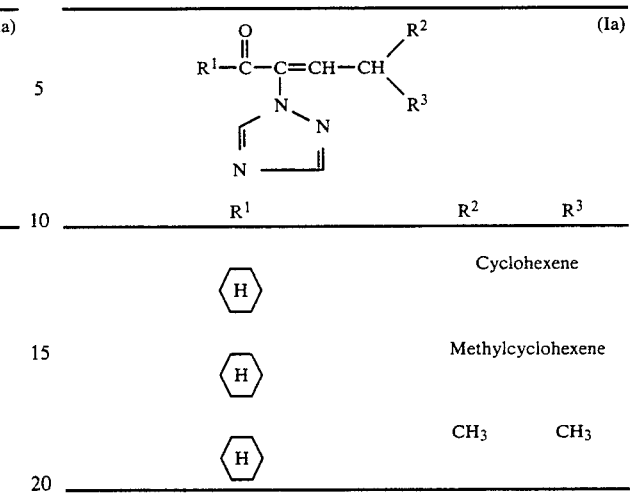

| R¹ | R² | R³ |
|---|---|---|
| phenyl | | Cyclohexene |
| phenyl | | Methylcyclohexene |
| phenyl | CH₃ | CH₃ |

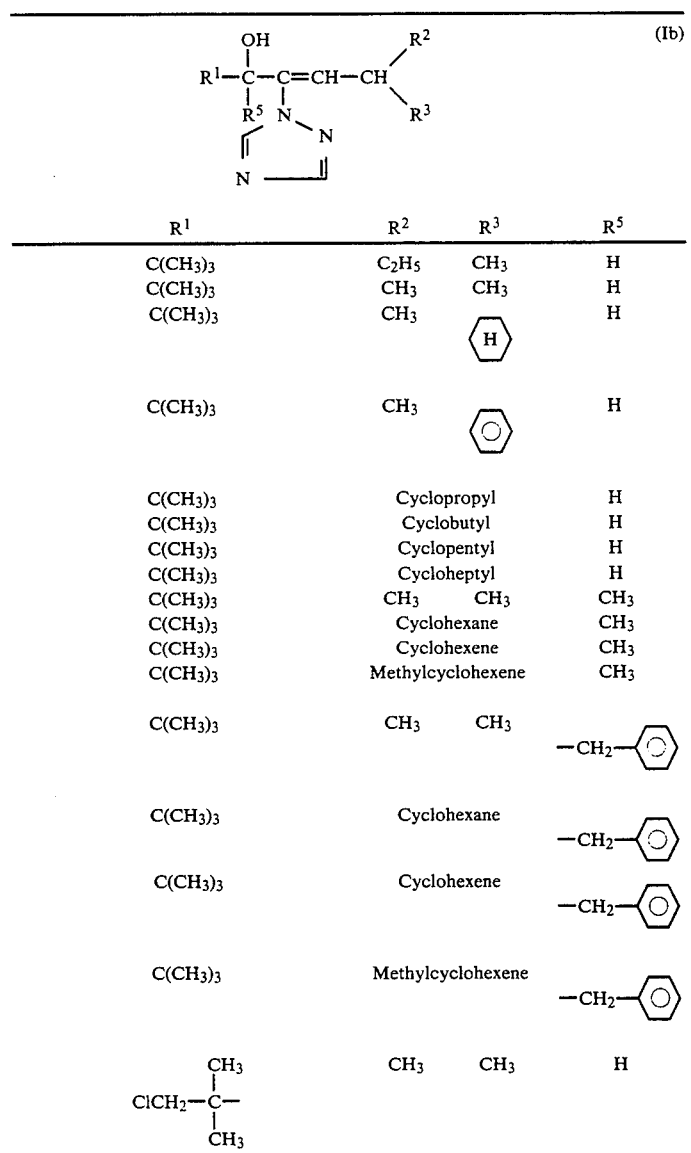

| R¹ | R² | R³ | R⁵ |
|---|---|---|---|
| C(CH₃)₃ | C₂H₅ | CH₃ | H |
| C(CH₃)₃ | CH₃ | CH₃ | H |
| C(CH₃)₃ | CH₃ | cyclohexyl | H |
| C(CH₃)₃ | CH₃ | phenyl | H |
| C(CH₃)₃ | Cyclopropyl | | H |
| C(CH₃)₃ | Cyclobutyl | | H |
| C(CH₃)₃ | Cyclopentyl | | H |
| C(CH₃)₃ | Cycloheptyl | | H |
| C(CH₃)₃ | CH₃ | CH₃ | CH₃ |
| C(CH₃)₃ | Cyclohexane | | CH₃ |
| C(CH₃)₃ | Cyclohexene | | CH₃ |
| C(CH₃)₃ | Methylcyclohexene | | CH₃ |
| C(CH₃)₃ | CH₃ | CH₃ | —CH₂—phenyl |
| C(CH₃)₃ | Cyclohexane | | —CH₂—phenyl |
| C(CH₃)₃ | Cyclohexene | | —CH₂—phenyl |
| C(CH₃)₃ | Methylcyclohexene | | —CH₂—phenyl |
| ClCH₂—C(CH₃)₂— | CH₃ | CH₃ | H |

-continued $$\begin{array}{c} \text{OH} \\ | \\ R^1-C-C=CH-CH \\ | \quad | \quad \quad \quad \quad \backslash \\ R^5 \quad N \quad \quad \quad \quad R^3 \\ \quad \quad \| \\ \quad \quad N \end{array} \begin{array}{c} R^2 \\ \\ \\ \\ \end{array}$$ (Ib)

with pyrazole ring (N–N) attached.

| R¹ | R² | R³ | R⁵ |
|---|---|---|---|
| ClCH₂–C(CH₃)(CH₃)– | Cyclohexane | | H |
| ClCH₂–C(CH₃)(CH₃)– | Cyclohexene | | H |
| ClCH₂–C(CH₃)(CH₃)– | Methylcyclohexene | | H |
| BrCH₂–C(CH₃)(CH₃)– | CH₃ | CH₃ | H |
| BrCH₂–C(CH₃)(CH₃)– | Cyclohexane | | H |
| BrCH₂–C(CH₃)(CH₃)– | Cyclohexene | | H |
| BrCH₂–C(CH₃)(CH₃)– | Methylcyclohexene | | H |
| FCH₂–C(CH₃)(CH₃)– | CH₃ | CH₃ | H |
| FCH₂–C(CH₃)(CH₃)– | Cyclohexane | | H |
| FCH₂–C(CH₃)(CH₃)– | Cyclohexene | | H |
| FCH₂–C(CH₃)(CH₃)– | Methylcyclohexene | | H |
| CH₃–C(CH₂Cl)(CH₂Cl)– | CH₃ | CH₃ | H |

-continued $$\begin{array}{c} \text{OH} \quad R^2 \\ R^1-\underset{\underset{R^5}{|}}{\overset{|}{C}}-\underset{\underset{N}{|}}{\overset{|}{C}}=CH-\underset{R^3}{\overset{|}{CH}} \\ \quad\quad N\diagdown_N\diagup \\ \quad\quad\quad N\!\!=\!\!\diagup \end{array} \qquad (Ib)$$

| $R^1$ | $R^2$ | $R^3$ | $R^5$ |
|---|---|---|---|
| $CH_3-\underset{\underset{CH_2Cl}{|}}{\overset{\overset{CH_2Cl}{|}}{C}}-$ | Cyclohexane | | H |
| $CH_3-\underset{\underset{CH_2Cl}{|}}{\overset{\overset{CH_2Cl}{|}}{C}}-$ | Cyclohexene | | H |
| $CH_3-\underset{\underset{CH_2Cl}{|}}{\overset{\overset{CH_2Cl}{|}}{C}}-$ | Methylcyclohexene | | H |
| $CH_3-SO_2-O-CH_2-\underset{\underset{CH_3}{|}}{\overset{\overset{CH_3}{|}}{C}}-$ | $CH_3$ | $CH_3$ | H |
| $CH_3-SO_2-O-CH_2-\underset{\underset{CH_3}{|}}{\overset{\overset{CH_3}{|}}{C}}-$ | Cyclohexane | | H |
| $CH_3-SO_2-O-CH_2-\underset{\underset{CH_3}{|}}{\overset{\overset{CH_3}{|}}{C}}-$ | Cyclohexene | | H |
| $CH_3-SO_2-O-CH_2-\underset{\underset{CH_3}{|}}{\overset{\overset{CH_3}{|}}{C}}-$ | Methylcyclohexene | | H |
| $CH_3-\!\!\bigcirc\!\!-SO_2-O-CH_2-\underset{\underset{CH_3}{|}}{\overset{\overset{CH_3}{|}}{C}}-$ | $CH_3$ | $CH_3$ | H |
| $CH_3-\!\!\bigcirc\!\!-SO_2-O-CH_2-\underset{\underset{CH_3}{|}}{\overset{\overset{CH_3}{|}}{C}}-$ | Cyclohexane | | H |
| $CH_3-\!\!\bigcirc\!\!-SO_2-O-CH_2-\underset{\underset{CH_3}{|}}{\overset{\overset{CH_3}{|}}{C}}-$ | Cyclohexene | | H |
| $CH_3-\!\!\bigcirc\!\!-SO_2-O-CH_2-\underset{\underset{CH_3}{|}}{\overset{\overset{CH_3}{|}}{C}}-$ | Methylcyclohexene | | H |
| $CH_3-CO-O-CH_2-\underset{\underset{CH_3}{|}}{\overset{\overset{CH_3}{|}}{C}}-$ | $CH_3$ | $CH_3$ | H |

-continued

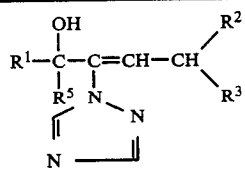

(Ib)

| R¹ | R² | R³ | R⁵ |
|---|---|---|---|
| CH₃—CO—O—CH₂—C(CH₃)(CH₃)— | Cyclohexane | | H |
| CH₃—CO—O—CH₂—C(CH₃)(CH₃)— | Cyclohexene | | H |
| CH₃—CO—O—CH₂—C(CH₃)(CH₃)— | Methylcyclohexene | | H |
| cyclohexyl | CH₃ | CH₃ | H |
| cyclohexyl | Cyclohexane | | H |
| cyclohexyl | Cyclohexene | | H |
| cyclohexyl | Methylcyclohexene | | H |
| phenyl | CH₃ | CH₃ | H |
| phenyl | Cyclohexane | | H |
| phenyl | Cyclohexene | | H |
| phenyl | Methylcyclohexene | | H |
| 4-chlorophenyl | CH₃ | CH₃ | H |
| 4-chlorophenyl | Cyclohexane | | H |
| 4-chlorophenyl | Cyclohexene | | H |
| 4-chlorophenyl | Methylcyclohexene | | H |
| 2,4-dichlorophenyl | CH₃ | CH₃ | H |

-continued

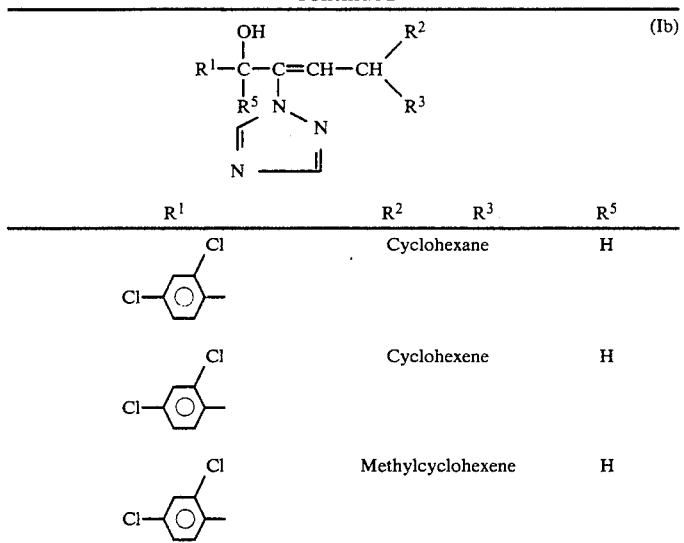

(Ib)

| R¹ | R² R³ | R⁵ |
|---|---|---|
| 2,4-dichlorophenyl | Cyclohexane | H |
| 2,4-dichlorophenyl | Cyclohexene | H |
| 2,4-dichlorophenyl | Methylcyclohexene | H |

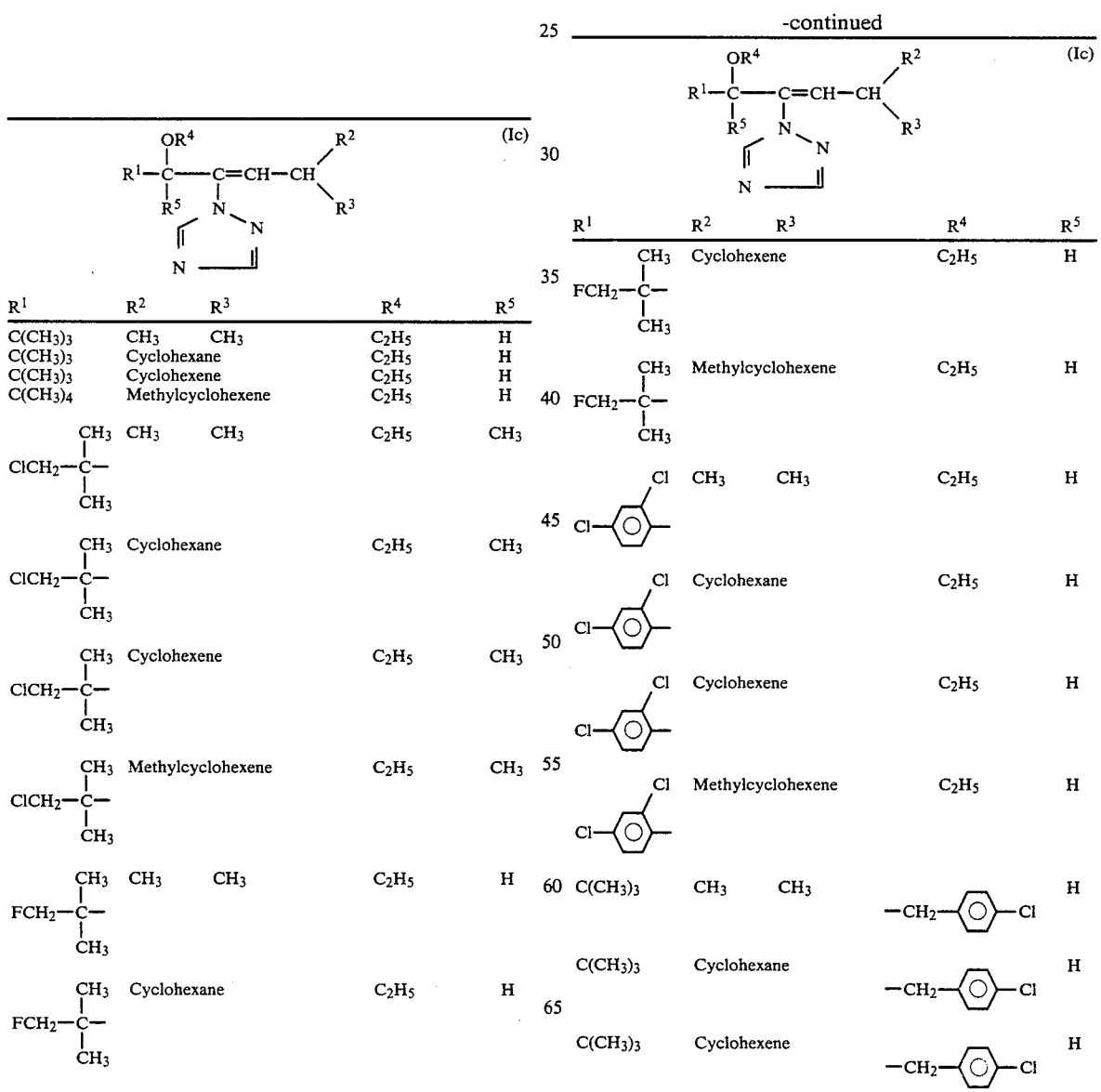

(Ic)

| R¹ | R² | R³ | R⁴ | R⁵ |
|---|---|---|---|---|
| C(CH₃)₃ | CH₃ | CH₃ | C₂H₅ | H |
| C(CH₃)₃ | Cyclohexane | | C₂H₅ | H |
| C(CH₃)₃ | Cyclohexene | | C₂H₅ | H |
| C(CH₃)₄ | Methylcyclohexene | | C₂H₅ | H |
| ClCH₂-C(CH₃)₂- | CH₃ | CH₃ | C₂H₅ | CH₃ |
| ClCH₂-C(CH₃)₂- | Cyclohexane | | C₂H₅ | CH₃ |
| ClCH₂-C(CH₃)₂- | Cyclohexene | | C₂H₅ | CH₃ |
| ClCH₂-C(CH₃)₂- | Methylcyclohexene | | C₂H₅ | CH₃ |
| FCH₂-C(CH₃)₂- | CH₃ | CH₃ | C₂H₅ | H |
| FCH₂-C(CH₃)₂- | Cyclohexane | | C₂H₅ | H |
| FCH₂-C(CH₃)₂- | Cyclohexene | | C₂H₅ | H |
| FCH₂-C(CH₃)₂- | Methylcyclohexene | | C₂H₅ | H |
| 2,4-dichlorophenyl | CH₃ | CH₃ | C₂H₅ | H |
| 2,4-dichlorophenyl | Cyclohexane | | C₂H₅ | H |
| 2,4-dichlorophenyl | Cyclohexene | | C₂H₅ | H |
| 2,4-dichlorophenyl | Methylcyclohexene | | C₂H₅ | H |
| C(CH₃)₃ | CH₃ | CH₃ | -CH₂-(4-chlorophenyl) | H |
| C(CH₃)₃ | Cyclohexane | | -CH₂-(4-chlorophenyl) | H |
| C(CH₃)₃ | Cyclohexene | | -CH₂-(4-chlorophenyl) | H |

-continued $$R^1-\underset{\underset{R^5}{|}}{\overset{\overset{OR^4}{|}}{C}}-\underset{\underset{\underset{\underset{N}{\overset{\|}{}}}{N}}{|}}{C}=CH-CH\underset{R^3}{\overset{R^2}{<}} \quad (Ic)$$

| R¹ | R² | R³ | R⁴ | R⁵ |
|---|---|---|---|---|
| C(CH₃)₃ | Methylcyclohexene | | —CH₂—C₆H₄—Cl | H |
| ClCH₂—C(CH₃)₂— | CH₃ | CH₃ | —CH₂—C₆H₄—Cl | H |
| ClCH₂—C(CH₃)₂— | Cyclohexane | | —CH₂—C₆H₄—Cl | H |
| ClCH₂—C(CH₃)₂— | Cyclohexene | | —CH₂—C₆H₄—Cl | H |
| ClCH₂—C(CH₃)₂— | Methylcyclohexene | | —CH₂—C₆H₄—Cl | H |
| FCH₂—C(CH₃)₂— | CH₃ | CH₃ | —CH₂—C₆H₄—Cl | H |
| FCH₂—C(CH₃)₂— | Cyclohexane | | —CH₂—C₆H₄—Cl | H |
| FCH₂—C(CH₃)₂— | Cyclohexene | | —CH₂—C₆H₄—Cl | H |
| FCH₂—C(CH₃)₂— | Methylcyclohexene | | —CH₂—C₆H₄—Cl | H |
| 2,4-Cl₂—C₆H₃— | CH₃ | CH₃ | —CH₂—C₆H₄—Cl | H |
| 2,4-Cl₂—C₆H₃— | Cyclohexane | | —CH₂—C₆H₄—Cl | H |
| 2,4-Cl₂—C₆H₃— | Cyclohexene | | —CH₂—C₆H₄—Cl | H |
| 2,4-Cl₂—C₆H₃— | Methylcyclohexene | | —CH₂—C₆H₄—Cl | H |
| ClCH₂—C(CH₃)₂— | CH₃ | CH₃ | —CO—CH₃ | H |
| ClCH₂—C(CH₃)₂— | Cyclohexane | | —CO—CH₃ | H |
| ClCH₂—C(CH₃)₂— | Cyclohexene | | —CO—CH₃ | H |
| ClCH₂—C(CH₃)₂— | Methylcyclohexene | | —CO—CH₃ | H |
| FCH₂—C(CH₃)₂— | CH₃ | CH₃ | —CO—CH₃ | H |
| FCH₂—C(CH₃)₂— | Cyclohexane | | —CO—CH₃ | H |
| FCH₂—C(CH₃)₂— | Cyclohexene | | —CO—CH₃ | H |
| FCH₂—C(CH₃)₂— | Methylcyclohexene | | —CO—CH₃ | H |
| 2,4-Cl₂—C₆H₃— | CH₃ | CH₃ | —CO—CH₃ | H |
| 2,4-Cl₂—C₆H₃— | Cyclohexane | | —CO—CH₃ | H |
| 2,4-Cl₂—C₆H₃— | Cyclohexene | | —CO—CH₃ | H |
| 2,4-Cl₂—C₆H₃— | Methylcyclohexene | | —CO—CH₃ | H |
| ClCH₂—C(CH₃)₂— | CH₃ | CH₃ | —CO—NHCH₃ | H |

-continued $$R^1-\underset{\underset{R^5}{|}}{\overset{\overset{OR^4}{|}}{C}}=CH-CH\underset{R^3}{\overset{R^2}{<}}\quad\text{(Ic)}$$

with pyrazole ring attached at $R^5$ position (N-N=CH-CH=)

| $R^1$ | $R^2$ | $R^3$ | $R^4$ | $R^5$ |
|---|---|---|---|---|
| ClCH$_2$-C(CH$_3$)$_2$- | Cyclohexane | | -CO-NHCH$_3$ | H |
| ClCH$_2$-C(CH$_3$)$_2$- | Cyclohexene | | -CO-NHCH$_3$ | H |
| ClCH$_2$-C(CH$_3$)$_2$- | Methylcyclohexene | | -CO-NHCH$_3$ | H |
| FCH$_2$-C(CH$_3$)$_2$- | CH$_3$ | CH$_3$ | -CO-NHCH$_3$ | H |
| FCH$_2$-C(CH$_3$)$_2$- | Cyclohexane | | -CO-NHCH$_3$ | H |
| FCH$_2$-C(CH$_3$)$_2$- | Cyclohexene | | -CO-NHCH$_3$ | H |
| FCH$_2$-C(CH$_3$)$_2$- | Methylcyclohexene | | -CO-NHCH$_3$ | H |
| 2,4-Cl$_2$-C$_6$H$_3$- | CH$_3$ | CH$_3$ | -CO-NHCH$_3$ | H |
| 2,4-Cl$_2$-C$_6$H$_3$- | Cyclohexane | | -CO-NHCH$_3$ | H |
| 2,4-Cl$_2$-C$_6$H$_3$- | Cyclohexene | | -CO-NHCH$_3$ | H |
| 2,4-Cl$_2$-C$_6$H$_3$- | Methylcyclohexene | | -CO-NHCH$_3$ | H |
| ClCH$_2$-C(CH$_3$)$_2$- | CH$_3$ | CH$_3$ | -CO-NH-C$_6$H$_5$ | H |
| ClCH$_2$-C(CH$_3$)$_2$- | Cyclohexane | | -CO-NH-C$_6$H$_5$ | H |
| ClCH$_2$-C(CH$_3$)$_2$- | Cyclohexene | | -CO-NH-C$_6$H$_5$ | H |
| ClCH$_2$-C(CH$_3$)$_2$- | Methylcyclohexene | | -CO-NH-C$_6$H$_5$ | H |
| FCH$_2$-C(CH$_3$)$_2$- | CH$_3$ | CH$_3$ | -CO-NH-C$_6$H$_5$ | H |
| FCH$_2$-C(CH$_3$)$_2$- | Cyclohexane | | -CO-NH-C$_6$H$_5$ | H |
| FCH$_2$-C(CH$_3$)$_2$- | Cyclohexene | | -CO-NH-C$_6$H$_5$ | H |
| FCH$_2$-C(CH$_3$)$_2$- | Methylcyclohexene | | -CO-NH-C$_6$H$_5$ | H |
| 2,4-Cl$_2$-C$_6$H$_3$- | CH$_3$ | CH$_3$ | -CO-NH-C$_6$H$_5$ | H |
| 2,4-Cl$_2$-C$_6$H$_3$- | Cyclohexane | | -CO-NH-C$_6$H$_5$ | H |
| 2,4-Cl$_2$-C$_6$H$_3$- | Cyclohexene | | -CO-NH-C$_6$H$_5$ | H |
| 2,4-Cl$_2$-C$_6$H$_3$- | Methylcyclohexene | | -CO-NH-C$_6$H$_5$ | H |
| ClCH$_2$-C(CH$_3$)$_2$- | CH$_3$ | CH$_3$ | -CO-C$_6$H$_5$ | H |
| ClCH$_2$-C(CH$_3$)$_2$- | Cyclohexane | | -CO-C$_6$H$_5$ | H |
| ClCH$_2$-C(CH$_3$)$_2$- | Cyclohexene | | -CO-C$_6$H$_5$ | H |

-continued

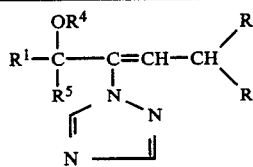 (Ic)

| R¹ | R² | R³ | R⁴ | R⁵ |
|---|---|---|---|---|
| ClCH₂-C(CH₃)₂- | Methylcyclohexene | | -CO-C₆H₅ | H |
| FCH₂-C(CH₃)₂- | CH₃ | CH₃ | -CO-C₆H₅ | H |
| FCH₂-C(CH₃)₂- | Cyclohexane | | -CO-C₆H₅ | H |
| FCH₂-C(CH₃)₂- | Cyclohexene | | -CO-C₆H₅ | H |
| FCH₂-C(CH₃)₂- | Methylcyclohexene | | -CO-C₆H₅ | H |
| 2,4-Cl₂C₆H₃- | CH₃ | CH₃ | -CO-C₆H₅ | H |
| 2,4-Cl₂C₆H₃- | Cyclohexane | | -CO-C₆H₅ | H |
| 2,4-Cl₂C₆H₃- | Cyclohexene | | -CO-C₆H₅ | H |
| 2,4-Cl₂C₆H₃- | Methylcyclohexene | | -CO-C₆H₅ | H |
| ClCH₂-C(CH₃)₂- | CH₃ | CH₃ | -CO-CHCl₂ | H |
| ClCH₂-C(CH₃)₂- | Cyclohexane | | -CO-CHCl₂ | H |
| ClCH₂-C(CH₃)₂- | Cyclohexene | | -CO-CHCl₂ | H |
| ClCH₂-C(CH₃)₂- | Methylcyclohexene | | -CO-CHCl₂ | H |

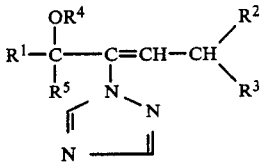 (Ic)

| R¹ | R² | R³ | R⁴ | R⁵ |
|---|---|---|---|---|
| FCH₂-C(CH₃)₂- | CH₃ | CH₃ | -CO-CHCl₂ | H |
| FCH₂-C(CH₃)₂- | Cyclohexane | | -CO-CHCl₂ | H |
| FCH₂-C(CH₃)₂- | Cyclohexene | | -CO-CHCl₂ | H |
| FCH₂-C(CH₃)₂- | Methylcyclohexene | | -CO-CHCl₂ | H |
| 2,4-Cl₂C₆H₃- | CH₃ | CH₃ | -CO-CHCl₂ | H |
| 2,4-Cl₂C₆H₃- | Cyclohexane | | -CO-CHCl₂ | H |
| 2,4-Cl₂C₆H₃- | Cyclohexene | | -CO-CHCl₂ | H |
| 2,4-Cl₂C₆H₃- | Methylcyclohexene | | -CO-CHCl₂ | H |
| C(CH₃)₃ | CH₃ | CH₃ | -CO-CH₃ | H |
| C(CH₃)₃ | Cyclohexane | | -CO-CH₃ | H |
| C(CH₃)₃ | Cyclohexene | | -CO-CH₃ | H |
| C(CH₃)₃ | Methylcyclohexene | | -CO-CH₃ | H |
| C(CH₃)₃ | CH₃ | CH₃ | -CO-NHCH₃ | H |
| C(CH₃)₃ | Cyclohexane | | -CO-NHCH₃ | H |
| C(CH₃)₃ | Cyclohexene | | -CO-NHCH₃ | H |
| C(CH₃)₃ | Methylcyclohexene | | -CO-NHCH₃ | H |
| C(CH₃)₃ | CH₃ | CH₃ | -CO-NH-C₆H₅ | H |
| C(CH₃)₃ | Cyclohexane | | -CO-NH-C₆H₅ | H |
| C(CH₃)₃ | Cyclohexene | | -CO-NH-C₆H₅ | H |
| C(CH₃)₃ | Methylcyclohexene | | -CO-NH-C₆H₅ | H |
| C(CH₃)₃ | CH₃ | CH₃ | -CO-C₆H₅ | H |

-continued

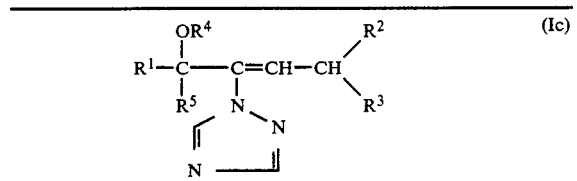

| R¹ | R² | R³ | R⁴ | R⁵ |
|---|---|---|---|---|
| C(CH₃)₃ | Cyclohexane | | —CO—⌬ | H |
| C(CH₃)₃ | Cyclohexane | | —CO—⌬ | H |
| C(CH₃)₃ | Methylcyclohexene | | —CO—⌬ | H |
| C(CH₃)₃ | CH₃ | CH₃ | —CO—CHCl₂ | H |
| C(CH₃)₃ | Cyclohexane | | —CO—CHCl₂ | H |
| C(CH₃)₃ | Cyclohexene | | —CO—CHCl₂ | H |
| C(CH₃)₃ | Methylcyclohexene | | —CO—CHCl₂ | H |

Other preferred compounds according to the invention are the addition products of acids and those 1-vinyltriazole derivatives of the formula (I) in which R¹, R², R³ and X have the meanings which have already been mentioned as preferred therefor.

Preferred acids which can be added on include hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

Further preferred compounds according to the invention are addition products of salts of metals of main groups II to IV and of sub-groups I and II and IV to VIII and those 1-vinyltriazole derivatives of the formula (I) in which R¹, R², R³ and X have the meanings which have already been mentioned as preferred therefor. Salts of copper, zinc, manganese, magnesium, tin, iron and nickel are particularly preferred. Possible anions of these salts are those which are derived from acids which lead to physiologically acceptable addition products. Such acids which are particularly preferred in this connection are the hydrogen halide acids (for example hydrochloric acid and hydrobromic acid), phosphoric acid, nitric acid and sulphuric acid.

If, for example, pinacolyl-1,2,4-triazole and cyclohexanecarbaldehyde are used as starting materials, the course of the reaction in process variant (a) can be represented by the following equation:

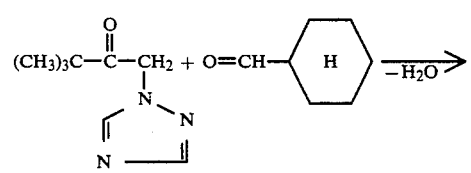

If 1-cyclohexyl-4,4-dimethyl-2-(1,2,4-triazol-1-yl)-pent-1-en-3-one and sodium borohydride are used as starting materials, the course of the reaction in process variant (b)(α) can be represented by the following equation:

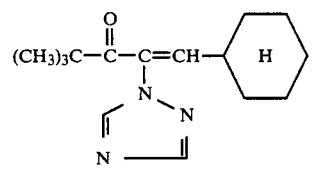

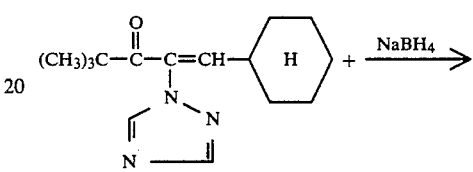

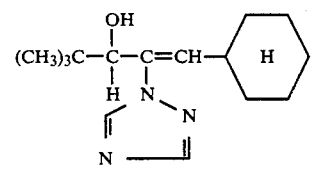

If 1-cyclohexyl-4,4-dimethyl-2-(1,2,4-triazol-1-yl)-pent-1-en-3-one and methyl-magnesium bromide are used as starting materials, the course of the reaction in process variant (b)(β) can be represented by the following equation:

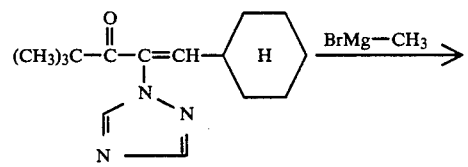

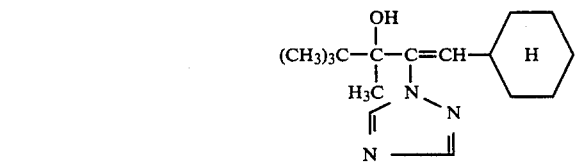

If 1-cyclohexyl-4,4-dimethyl-1-(1,2,4-triazol-1-yl)-pent-1-en-3-ol and ethyl bromide are used as starting materials and sodium hydride is used as the base, the course of the reaction in process variant (c) can be represented by the following equation:

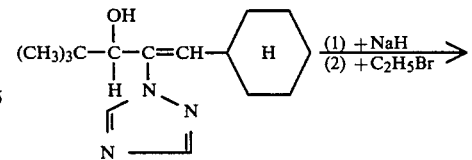

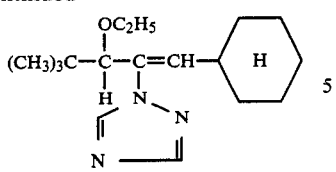

If 1-cyclohexyl-4,4-dimethyl-2-(1,2,4-triazol-1-yl)-pent-1-en-3-ol and acetyl chloride are used as starting materials and sodium hydride is used as the base, the course of the reaction in process variant (c) can be represented by the following equation:

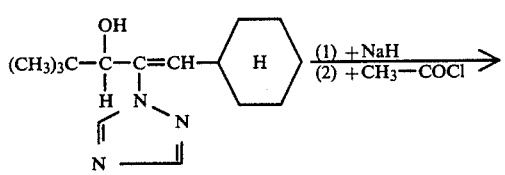

If 1-cyclohexyl-4,4-dimethyl-2-(1,2,4-triazol-1-yl)-pent-1-en-3-ol and acetic anhydride are used as starting materials, the course of the reaction in process variant (d) can be represented by the following equation:

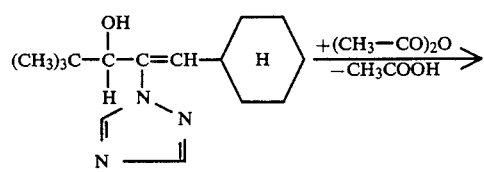

If 1-cyclohexyl-4,4-dimethyl-2-(1,2,4-triazol-1-yl)-pent-1-en-3-ol and phenyl isocyanate are used as starting materials, the course of the reaction in process variant (e) can be represented by the following equation:

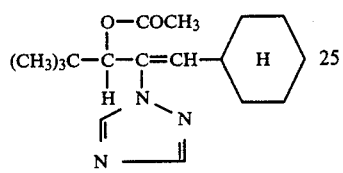

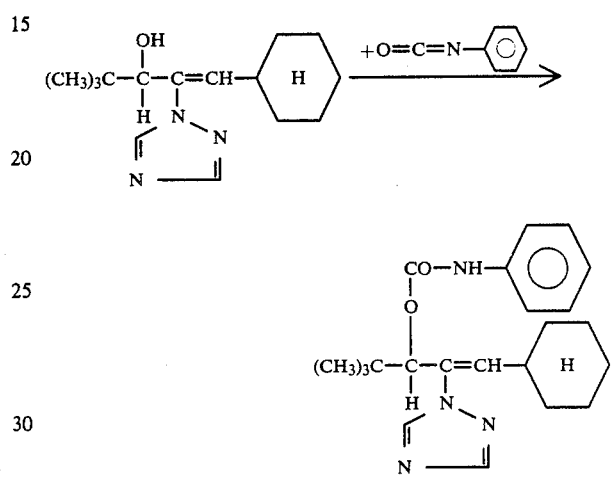

The formula (II) provides a general definition of the triazole-ketones required as starting materials in carrying out process variant (a). In this formula, $R^1$ preferably has those meanings which have already been mentioned as preferred in connection with the description of the substances of the formula (I).

Most of the triazole-ketones of the formula (II) are known (see DE-OS (German Published Specification) No. 2,431,407, DE-OS (German Published Specification) No. 2,610,022 and DE-OS (German Published Specification) No. 2,638,470). The compounds of the formula (II) which have not hitherto been described in the literature can be prepared by customary methods. They are obtained by reacting the corresponding halo-ketones with 1,2,4-triazole in the presence of an acid-binding agent. The compounds of the following table may be mentioned as examples:

$$R^1-\overset{O}{\underset{\|}{C}}-CH_2-N\begin{array}{c}\diagup N\\ \diagdown N\end{array}\rightleftharpoons\qquad (II)$$

| $R^1$ | $R^1$ | $R^1$ |
|---|---|---|
| —C(CH₃)₃ | —CH(CH₃)₂ | —CH₃ |
| —C(CH₃)(CH₃)—CH₂Cl | —C(CH₃)(CH₃)—CH₂Br | —C(CH₃)(CH₃)—CH₂F |
| —C(CH₂Cl)(CH₃)—CH₂Cl | CH₃—SO₂—O—CH₂—C(CH₃)(CH₃)— | CH₃—⌬—SO₂—O—CH₂—C(CH₃)(CH₃)— |

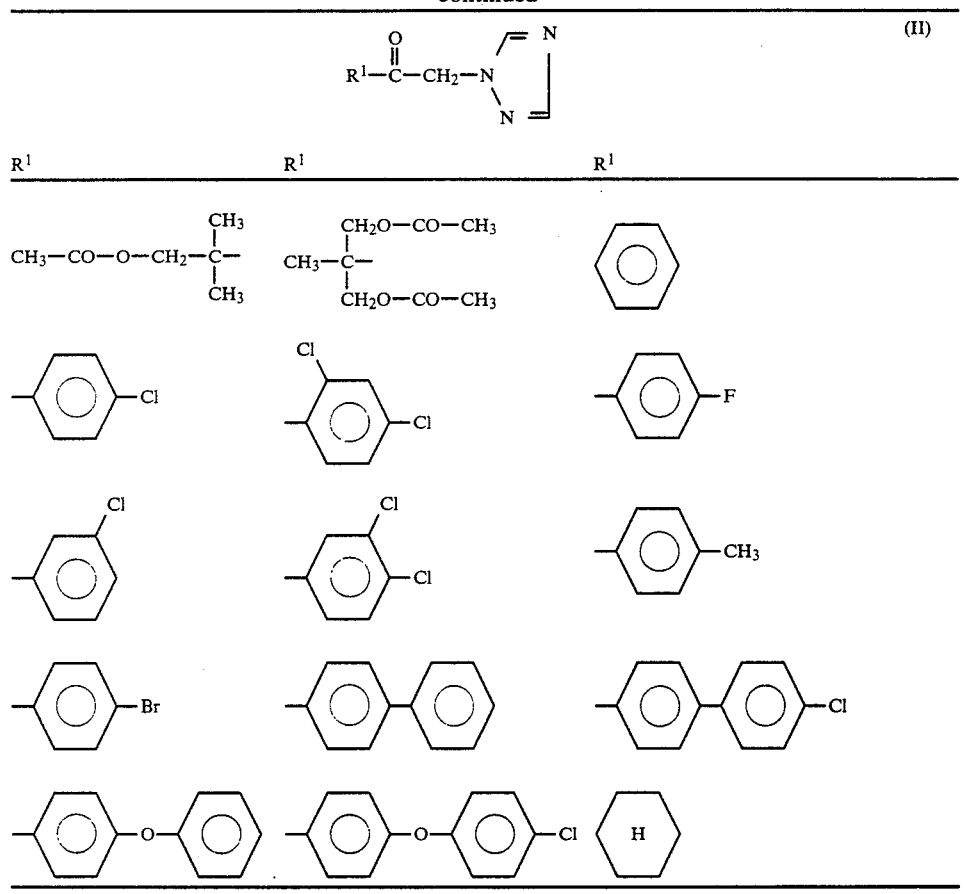

The formula (III) provides a general definition of the aldehydes also to be used as starting materials for process variant (a). In this formula, $R^2$ and $R^3$ preferably have those meanings which have already been mentioned as preferred in connection with the description of the substances of the formula (I).

The aldehydes of the formula (III) are generally known compounds of organic chemistry. The following compounds may be mentioned as examples:

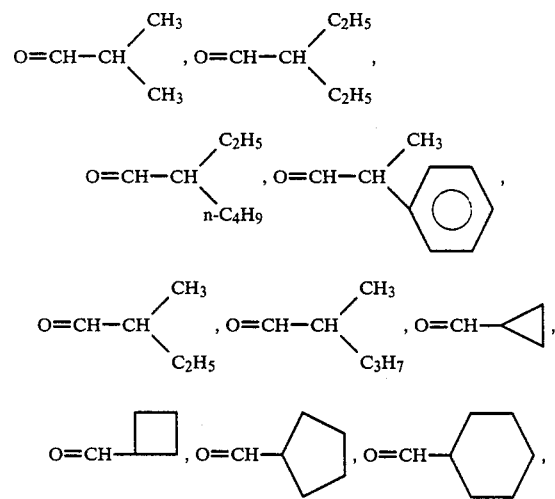

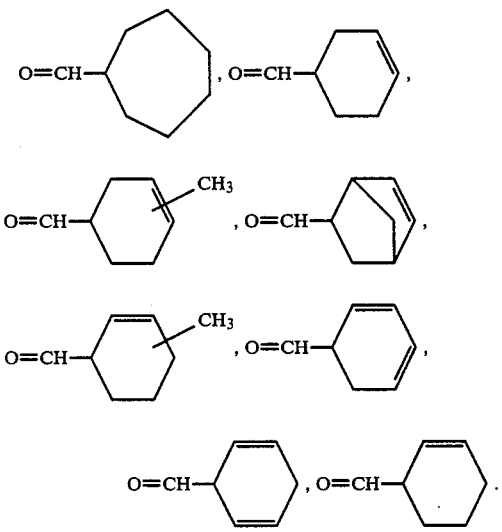

The formula (Ia) provides a general definition of the compounds to be used as starting materials for process variants (b) ($\alpha$) and (b) ($\beta$). In this formula, $R^1$, $R^2$ and $R^3$ preferably have those meanings which have already been mentioned as preferred in connection with the description of the substances of the formula (I).

Compounds of the formula (Ia) in which $R^1$ represents optionally substituted alkyl or cycloalkyl are according to the invention, whereas some of those in which $R^1$ represents optionally substituted aryl are known (see DE-OS (German Published Specification) No. 2,645,617).

The complex hydrides required as reaction components for process variant (b) (α) are generally known compounds of organic chemistry. Preferred examples which may be mentioned are sodium borohydride and lithium alanate.

The formula (IV) provides a general definition of the Grignard compounds also to be used as starting substances for process variant (b) (β). In this formula, $R^6$ preferably represents alkyl with 1 to 4 carbon atoms or aralkyl with 1 to 2 carbon atoms in the alkyl part and 6 to 10 carbon atoms in the aryl part, benzyl being mentioned as an example, which is optionally substituted by halogen or alkyl with 1 to 4 carbon atoms. Hal preferably represents chlorine, bromine or iodine.

The Grignard compounds of the formula (IV) are generally known compounds of organic chemistry. Examples which may be mentioned are methyl-magnesium bromide, ethyl-magnesium bromide, isopropyl-magnesium bromide and benzyl-magnesium bromide.

The formula (Ib) provides a general definition of the 1-vinyltriazole derivatives to be used as starting materials for process variants (c), (d) and (e). In this formula $R^1$, $R^2$, $R^3$ and $R^5$ preferably have those meanings which have already been mentioned as preferred in connection with the description of the substances of the formula (I).

The formula (V) provides a general definition of the halides also to be used as starting materials for process variant (c). In this formula, $R^7$ preferably represents straight-chain or branched alkyl with 1 to 4 carbon atoms or aralkyl with 1 to 2 carbon atoms in the alkyl part and 6 to 10 carbon atoms in the aryl part, such as benzyl or naphthylmethyl, which is optionally monosubstituted or polysubstituted by identical or different substituents, preferred substituents being halogen, alkyl with 1 to 4 carbon atoms, haloalkyl with up to 2 carbon atoms and up to 3 identical or different halogen atoms, preferred halogen atoms being fluorine and chlorine, and phenyl and phenoxy, optionally substituted by halogen. $R^7$ furthermore preferably represents the acyl radical $—CO—R^{10}$ or the carbamoyl radical $—CO—NR^{11}R^{12}$, wherein $R^{10}$, $R^{11}$ and $R^{12}$ preferably have those meanings which have already been mentioned as preferred for these radicals in connection with the description of the substances according to the invention. Hal' in formula (V) preferably represents fluorine, chlorine or bromine.

The halides of the formula (V) are generally known compounds of organic chemistry.

The formula (VI) provides a general definition of the acid anhydrides also to be used as starting substances for process variant (d). In this formula, $R^8$ preferably represents the acyl radical of the formula $—CO—R^{10}$, wherein $R^{10}$ preferably has those meanings which have already been mentioned as preferred for this radical in connection with the description of the substances according to the invention.

The acid anhydrides of the formula (VI) are generally known compounds of organic chemistry.

The formula (VII) provides a general definition of the isocyanates also to be used as starting substances for process variant (e). In this formula, $R^9$ preferably represents alkyl with 1 to 8 carbon atoms, haloalkyl with up to 4 carbon atoms and up to 5 identical or different halogen atoms, such as, in particular, fluorine and chlorine atoms, aryl with 6 to 10 carbon atoms, such as phenyl and naphthyl, which is optionally monosubstituted or polysubstituted by identical or different substituents, preferred substituents being halogen, alkyl with 1 to 4 carbon atoms and haloalkyl with up to 2 carbon atoms and up to 5 identical or different halogen atoms, such as, in particular, fluorine and chlorine atoms, or preferably represents haloalkyl-mercapto with 1 to 2 carbon atoms and up to 5 halogen atoms, such as, in particular, fluorine and chlorine atoms.

The isocyanates of the formula (VII) are generally known compounds of organic chemistry.

Preferred solvents for process variant (a) of the invention are inert organic solvents. These include, as preferences, alcohols, such as methanol and ethanol; ethers, such as tetrahydrofuran and dioxan; aliphatic and cycloaliphatic hydrocarbons, such as hexane and cyclohexane; aromatic hydrocarbons, such as benzene, toluene and cumene; and halogenated aliphatic and aromatic hydrocarbons, such as methylene chloride, carbon tetrachloride, chloroform, chlorobenzene and dichlorobenzene.

Process variant (a) is carried out in the presence of a catalyst. Any of the acid and, especially, basic catalysts, and buffer mixtures thereof, which can customarily be used can be employed. These catalysts include, as preferences, Lewis acids, for example boron trifluoride, boron trichloride, tin tetrachloride or titanium tetrachloride; organic bases, such a pyridine and piperidine; and, especially, piperidine acetate.

The reaction temperatures can be varied within a substantial range in carrying out process variant (a). In general, the reaction is carried out at from 20° to 160° C., preferably at the boiling point of the particular solvent.

In carrying out process variant (a), 1 to 1.5 moles of aldehyde of the formula (III) and a catalytic amount to 0.2 mole of catalyst are employed per mole of triazoleketone of the formula (II). To isolate the compounds of the formula (I), the two reaction products, which are isomeric with regard to the position of the double bond, are separated by customary methods, for example by salt formation (see the preparative examples) or by chromatography. Unambiguous allocation of structure is effected on the basis of spectroscopic data, in particular the NMR data.

Preferred solvents for process variant (b) (α) are polar organic solvents. These include, as preferences, alcohols, such as methanol, ethanol, isopropanol or butanol; and ethers, such as diethyl ether or tetrahydrofuran.

The reaction temperatures can be varied within a substantial range in carrying out process variant (b) (α). In general, the reaction is carried out at from 0° to 30° C., preferably at from 0° to 20° C.

Equivalent amounts of starting materials are preferably used for carrying out process variant (b) (α). To isolate the compound of the formula (I), the reaction mixture is taken up in dilute hydrochloric acid and extracted with an organic solvent. Further working up is effected in the customary manner.

Preferred solvents for process variant (b) (β) are anhydrous ethers, such as diethyl ether, dibutyl ether or tetrahydrofuran.

The reaction temperatures can be varied within a substantial range in carrying out process variant (b) (β). In general, the reaction is carried out at from 0° to 80° C., preferably from 30° to 60° C.

Equivalent amounts of starting substances are preferably used for carrying out process variant (b) (β). Isolation of the compound of the formula (I) is effected in a customary and generally known manner.

Preferred solvents for process variant (c) are inert organic solvents. These include, as preferences, ethers, such as diethyl ether and dioxan; aromatic hydrocarbons, such as toluene and benzene (and in some cases, also chlorinated hydrocarbons, such as chloroform, methylene chloride or carbon tetrachloride); ketones, such as acetone or methyl ethyl ketone; and nitriles, such as acetonitrile. For reasons of simplicity, an acid halide employed can also be used as the solvent, whereupon an appropriate excess becomes necessary.

The reaction temperatures can be varied within a substantial range in carrying out process variant (c). In general, the reaction is carried out at from 20° to 150° C., preferably from 20° to 100° C., or at the boiling point of the particular solvent.

If appropriate, process variant (c) can be carried out in the presence of a strong base. Preferred strong bases include alkali metal hydrides, alkali metal amides and alkali metal alcoholates, for example sodium hydride, sodium amide and potassium tert.-butylate.

If appropriate, process variant (c) can be carried out in the presence of an acid-binding agent (hydrogen halide acceptor). Suitable acid-binding agents include organic bases, preferably tertiary amines, for example triethylamine; and furthermore inorganic bases, for example alkali metal hydroxides and alkali metal carbonates.

In carrying out process variant (c), 1 to 3 moles of halide of the formula (V) are preferably employed per mole of the compound of the formula (Ib). To isolate the end product, the reaction mixture is freed from solvent, and water and an organic solvent are added to the residue. The organic phase is separated off and worked up in the customary manner.

In a preferred embodiment, a procedure is appropriately followed in which a compound of the formula (Ib) is used as the starting material, this compound is converted into the alkenolate in a suitable inert organic solvent by means of an alkali metal hydride or alkali metal amide and the alkenolate is reacted immediately, without isolation, with a halide of the formula (V), the compound of the formula (I) being obtained in one operation with elimination of an alkali metal halide.

According to another preferred embodiment, the reaction of a halide of the formula (V), in which $R^7$ represents alkyl or optionally substituted aralkyl, in the above-mentioned preferred embodiment is carried out in a two-phase system, for example aqueous sodium hydroxide solution or potassium hydroxide solution/toluene or methylene chloride, with the addition of 0.01–1 mole of a phase transfer catalyst, for example an ammonium or phosphonium compound, for example benzyl-dodecyl-dimethyl-ammonium chloride (Zephirol) or triethyl-benzyl-ammonium chloride.

Preferred solvents for process variant (d) are inert organic solvents. These include, as preferences, the solvents listed in the case of process variant (c) and the particular acid anhydrides of the formula (VI) used.

Preferred catalysts which can be used in process variant (d) are any of the customary acid and basic catalysts, for example sulphuric acid, hydrogen chloride, hydrogen bromide, boron trifluoride, zinc chloride, sodium acetate, sodium benzoate, sodium carbonate, calcium oxide, magnesium oxide, pyridine and triethylamine.

The reaction temperatures can be varied within a substantial range in carrying out process variant (d). In general, the reaction is carried out at from 20° to 150° C., preferably from 50° to 120° C.

Equivalent amounts of starting materials are preferably used in carrying out process variant (d). For reasons of simplicity, the acid anhydride of the formula (VI) employed can also be used as the solvent, whereupon an appropriate excess becoms necessary. Isolation of the compound of the formula (I) is effected in the customary manner.

Preferred solvents for process variant (e) are inert organic solvents. These include, as preferences, the solvents listed in the case of process variant (c).

Preferred catalysts which can be used in process variant (e) are tertiary bases, such as triethylamine and pyridine, or organo-tin compounds, such as dibutyl-tin dilaurate and tributyl-tin laurate.

The reaction temperatures can be varied within a substantial range in carrying out process variant (e). In general, the reaction is carried out at from 0° to 100° C., preferably from 20° to 40° C.

Equivalent amounts of starting substances are preferably used in carrying out process variant (e). To isolate the compound of the formula (I), the solvent is distilled off and the residue is worked up by customary methods.

The compounds of the formula (I) can be converted into acid addition salts or metal salt complexes.

The following acids can preferably be used to prepare physiologically acceptable acid addition salts of the compounds of the formula (I): the hydrogen halide acids (for example hydrobromic acid and, especially, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalene-disulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can be used to prepare metal salt complexes of the compounds of the formula (I), examples of metals which may be mentioned being copper, zinc, manganese, magnesium, tin, iron and nickel.

Possible anions of the salts are preferably those which are derived from the following acids: hydrogen halide acids (for example hydrochloric acid and hydrobromic acid), phosphoric acid, nitric acid and sulphuric acid.

The metal complexes of compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and if appropriate by recrystallization.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds which can be used according to the invention can be employed with particularly good success for combating those fungi which cause powdery mildew diseases, especially for combating Erysiphe species, for example the powdery mildew of barley or cereal causative organism (*Erysiphe graminis*). It should be particularly emphasized that the active compounds according to the invention not only develop a protective action, but also have a systemic action. Thus, it is possible to protect plants against fungal attack when the active compound is fed to the above-ground parts of the plants via the soil and the root or via the seed.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such a kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkly sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellants, growth factors, plante nutrients and agents for improving soil structure, as well as other plant growth regulators.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts used can be varied within a substantial range. In general, 0.01 to 50 kg, preferably 0.05 to 10 kg, of the active compound are employed per hectare of soil surface.

When the substances according to the invention are used as fungicides, the amount used can also be varied within a substantial range, depending on the nature of the application. Thus, especially in the treatment of parts of plants, the active compound concentrations in the use forms are in general between 1 and 0.0001% by weight, especially between 0.5 and 0.001%. In the treatment of seed, amounts of active compound of 0.001 to 50 g, especially 0.01 to 10 g, are generally required per kilogram of seed. For the treatment of soil, active compound concentrations of 0.00001 to 0.1% by weight, especially 0.0001 to 0.02%, are generally required at the place of action.

The present invention also provides plant-growth regulating or fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth regulating and fungicidal activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

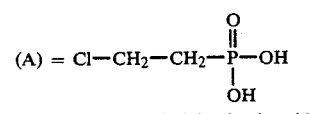
2-Chloroethylphophonic acid

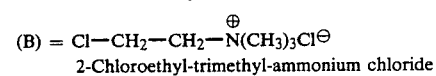
2-Chloroethyl-trimethyl-ammonium chloride

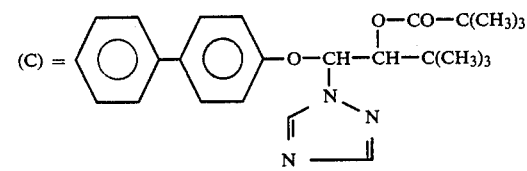

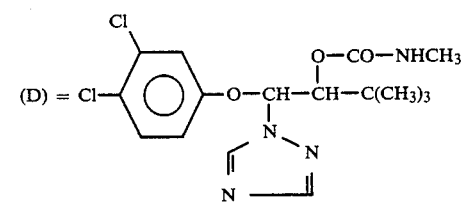

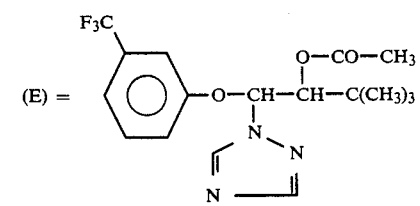

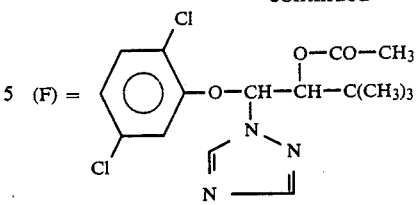

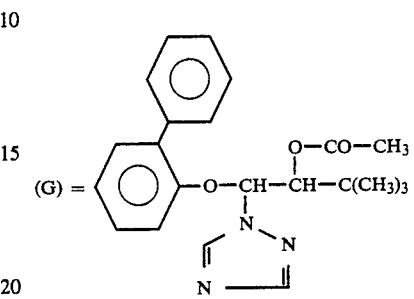

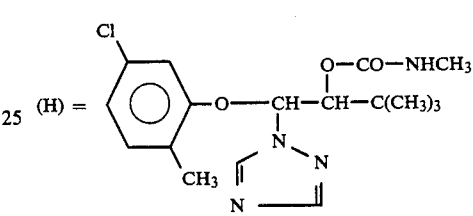

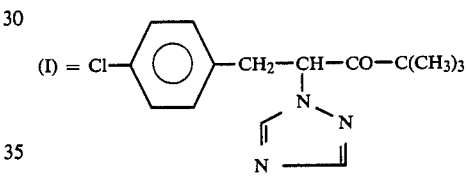

EXAMPLE A

Formation of ethylene
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. These were introduced into vessels which could be closed air-tight, together with 1 ml of the preparation of active compound or control solution. After 24 hours the ethylene which had collected in the vessels was determined by customary methods of detection. The evolution of ethylene from the pieces of leaf treated with the preparations of active compound was compared with the evolution of ethylene from the controls.

Compared with the control, active compound (3) caused a greatly increased evolution of ethylene.

EXAMPLE B

Inhibition of growth of barley
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. In this stage, the plants were sprayed with the preparation of active compound until dripping wet. After 3 weeks, the additional growth was measured on all plants and the inhibition of growth in percent of the additional growth of the control plants was calculated. 100% inhibition of growth meant that growth had stopped and 0% denoted a growth corresponding to that of the control plants.

In this test, active compounds (2), (3) and (12) exhibited a better inhibition of growth than substance (A) which is known from the prior art.

EXAMPLE C

Influence on growth of sugar-beet
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, whereas positive values characterized a promotion of growth in comparison to the control plants.

In this test, active compounds (2), (3), (4), (12), (14) and (16) influenced growth better than substance (B) which is known from the prior art.

EXAMPLE D

Inhibition of growth of soya beans
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

In this test, active compounds (2), (3), (12), (13), (14) and (16) exhibited a better inhibition of growth than substance (B) which is known from the prior art.

EXAMPLE E

Inhibition of growth of cotton
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, compared with the control, active compounds (2), (3), (4) and (12) exhibited a powerful inhibition of growth.

EXAMPLE F

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

In this test, for example, the following compounds exhibited a very good action, which was superior to that of the compounds (C), (D) and (E) known from the prior art: compounds (2), (3), (16), (4), (11) and (12).

EXAMPLE G

Powdery mildew of barley (*Erysiphe graminis* var. *hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordei* and grown on at 21-22 deg. C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The active compound was the more active, the lower was the degree of mildew infection.

In this test, for example, the following compounds exhibited a very good action which was superior to that of the compounds (F), (G) and (H) known from the prior art: compounds (2), (3), (4), (11) and (12).

EXAMPLE H

Mycelium growth test
Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Ratio of solvent mixture to nutrient medium:
  2 parts by weight of solvent mixture
  100 parts by weight of agar nutrient medium
Composition of the solvent mixture:
  0.19 part by weight of acetone or dimethylformamide
  0.01 part by weight of emulsifier (alkylaryl polyglycol ether)
  1.80 parts by weight of water The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg. C.) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 21 deg. C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:
  1 no growth
  up to 3 very strong inhibition of growth
  up to 5 medium inhibition of growth
  up to 7 slight inhibition of growth
  9 growth equal to that of untreated control.

As test organisms, the following fungi were employed:

In this test, for example, the following compounds exhibited a very good action which was superior to that of the compound (I) known from the prior art: compounds (2) and (3).

EXAMPLE I

Inhibition of growth of rice

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Rice plants were grown in a green-house to the 2-leaf stage in $10 \times 10 \times 10$ cm pots filled with earth. In this stage, the plants were sprayed with the preparations of active compound until dripping wet. After 10 days, the additional growth was measured on all plants and the inhibition of growth in percent of the additional growth of the control plants was calculated. 100% inhibition of growth meant that growth had stopped and 0% denoted a growth corresponding to that of the control plants.

In this test, active compound (2) exhibited a strong growth inhibiting activity.

EXAMPLE J

Inhibition of growth of water-rice (var. Nihonbare)

5 parts of active compound were mixed in a mixer with 2.5 parts of Newkalgen CP-50+), 30 parts of Bentonit and 62.5 parts of talkum. Then 20 parts of water were added. The pasty material was pressed through wholes of a diameter of 0.5 mm and then was dried. There was obtained a granulate having a corn size of a diameter of 0.5 mm and a length of 0.7 mm.

Ten days old rice plants were planted in containers having a size of $25 \times 20 \times 10$ cm, in which containers water is dammed up above the soil. After 10 days, the preparation of active compound was applied to the water. After an additional period of 14 days, the hight of the plants was measured.

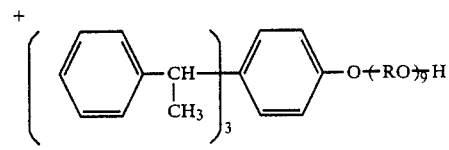

R=Ethylen or propylen in a ratio of 9:1.
In this test, the active compound (2) exhibited a very strong growth inhibiting activity.

Preparative examples

EXAMPLE 1

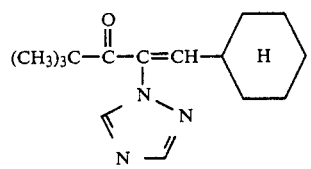

(1)

Process variant (a)

83.5 g (0.5 mol) of pinacolyl-1,2,4-triazole, 60 g (0.54 mol) of cyclohexanealdehyde, 4.2 g (0.05 mol) of piperidine and 6 g (0.1 mol) of glacial acetic acid in 300 ml of toluene were heated under reflux, using a water separator, until no further water passed over. After cooling the reaction solution, it was washed with saturated sodium chloride solution, the organic phase was dried over sodium sulphate and filtered and the filtrate was concentrated. The residue was taken up in 500 ml of acetone, and a filtered solution of 90 g (0.25 mol) of naphthalene-1,5-disulphonic acid in 500 ml of acetone was added, whilst stirring.

The precipitate which initially separated out was filtered off, the filtrate was concentrated further and the resulting colourless crystalline residue was taken up in 500 ml of methylene chloride. Thereafter, half-concentrated sodium carbonate solution was added until the mixture had an alkaline reaction. The organic phase was separated off, dried and filtered and the filtrate was concentrated. The oily residue was taken up in petroleum ether and the mixture was left to crystallise. 64 g (49% of theory) of 1-cyclohexyl-4,4-dimethyl-2-(1,2,4-triazol-1-yl)-pent-1-en-3-one of melting point 98° C. were obtained.

Preparation of the starting material

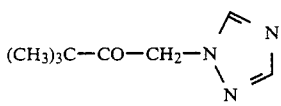

138 g (2 mol) of 1,2,4-triazole were added in portions to 276.4 g. (2 mol) of ground potassium carbonate and 269.2 g (2 mol) of α-chloropinacolin in 500 ml of acetone at room temperature, the internal temperature rising to the boiling point. The reaction mixture was stirred under reflux for 5 hours and then cooled to room temperature. It was filtered and the filtrate was concentrated by distilling off the solvent in vacuo. After adding benzene, the oily residue crystallised. 240.8 g (72% of theory) of 3,3-dimethyl-1-(1,2,4-triazol-1-yl)-butan-2-one of melting point 62°–64° C. were obtained.

EXAMPLE 2

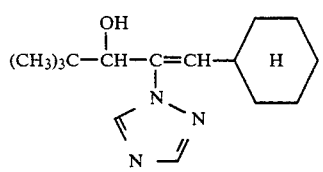

Process variant (b) (α):

26 g (0.1 mol) of 1-cyclohexyl-4,4-dimethyl-2-(1,2,4-triazol-1-yl)-pent-1-en-3-one (Example 1) were taken up in 200 ml of methanol, and 4.5 g of sodium borohydride were added in portions, whilst stirring and cooling. When the reaction had ended, the reaction mixture was adjusted to pH 6 and concentrated. The residue was taken up in 200 ml of methylene chloride, the methylene chloride mixture was washed with saturated sodium bicarbonate solution, dried over sodium sulphate and filtered and the filtrate was concentrated. The residue was recrystallised from petroleum ether. 14.5 g (55% of theory) of 1-cyclohexyl-4,4-dimethyl-2-(1,2,4-triazol-1-yl)-pen-1-en-3-ol of melting point 131° C. were obtained.

EXAMPLE 3

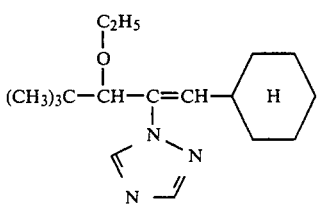

Process variant (c)

A solution of 26.3 g (0.1 mol) of 1-cyclohexyl-4,4-dimethyl-2-(1,2,4-triazol-1-yl)-pent-1-en-3-ol (Example 2) in 50 ml of dioxan was added dropwise to a suspension of 3 g of 80% strength sodium hydride in 100 ml of dioxan. When the addition had ended, the mixture was warmed to 50° C. for 1 hour. After cooling, 10.9 g (0.1 mol) of ethyl bromide were added dropwise and the reaction mixture was heated under reflux overnight. After cooling, 10 ml of methanol were added and the mixture was concentrated in a rotary evaporator. The residue was taken up in methylene chloride and the methylene chloride mixture was washed with water. After drying the organic phase over sodium sulphate, it was filtered and the filtrate was concentrated. The residue was distilled. 11.0 g (37.8% of theory) of 1-cyclohexyl-3-ethoxy-4,4-dimethyl-2-(1,2,4-triazol-1-yl)-pent-1-ene of boiling point 110° C./0.07 mm Hg were obtained.

EXAMPLE 4

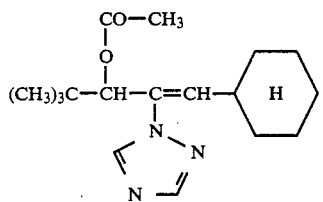

Process variant (c)

A solution of 13.15 g (0.05 mol) of 1-cyclohexyl-4,4-dimethyl-2-(1,2,4-triazol-1-yl)-pent-1-en-3-ol (Example 2) in 50 ml of dioxan was added dropwise to a suspension of 1.5 g of 80% strength sodium hydride in 50 ml of dioxan. When the evolution of hydrogen had ended, 3.9 g (0.05 mol) of acetyl chloride were added dropwise. The mixture was heated under reflux for 4 hours. After cooling the mixture, the solvent was distilled off in vacuo, the residue was taken up in methylene chloride and the methylene chloride mixture was extracted with water. The organic phase was dried over sodium sulphate and filtered and the solution was concentrated. The residue was purified over a column (silica gel; methanol: chloroform=1:3). 5.6 g (35.4% of theory) of 3-acetoxy-1-cyclohexyl-4,4-dimethyl-2-(1,2,4-triazol-1-yl)-pen-1-ene were obtained as a pale yellow oil.

Process variant (d)

2 ml of pyridine were added to a solution of 13.15 g (0.05 mol) of 1-cyclohexyl-4,4-dimethyl-2-(1,2,4-triazol-1-yl)-pent-1-en-3-ol (Example 2) in 100 ml of acetic anhydride. The mixture was stirred at 70° C. for 4 hours. Thereafter, the reaction mixture was poured onto water and neutralised with sodium bicarbonate. The aqueous phase was extracted several times with ether. The combined ether phases were dried over sodium sulphate and concentrated. 11.2 g (70.8% of theory) of 3-acetoxy-1-cyclohexyl-4,4-dimethyl-2-(1,2,4-triazol-1-yl)-pent-i-ene were obtained as a pale yellow oil.

EXAMPLE 5

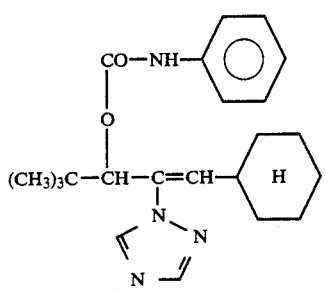
(5)

Process variant (e)

6.5 g (0.055 mol) of phenyl isocyanate and three drops of tributyl-tin laurate, as the catalyst, were added to a solution of 13.15 g (0.05 mol) of 1-cyclohexyl-4,4-dimethyl-2-(1,2,4-triazol-1-yl)-pent-1-en-3-ol (Example 2) in 100 ml of ether. The mixture was stirred at room temperature for 5 days. After distilling off the solvent in vacuo, the residue was recrystallised from ethyl acetate/ligroin. 4.8 g (25.1% of theory) of 1-cyclohexyl-4,4-dimethyl-3-phenylcarbamoyloxy-2-(1,2,4-triazol-1-yl)-pent-1-ene of melting point 156° C. were obtained.

The following compounds of Table 1 were obtained by procedures analogous to those described in the above Examples.

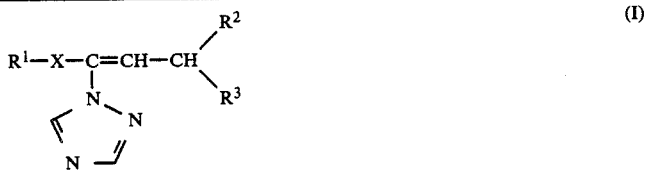
(I)

| Example No. | R¹ | X | R² | R³ | Melting point (°C.) |
|---|---|---|---|---|---|
| 6 | (CH₃)₃C | —CO— | cyclohexenyl | | 193 (x ½ NDS) |
| 7 | (CH₃)₃C | —CO— | cyclohexenyl | | 40–48 |
| 8 | (CH₃)₃C | —CO— | cyclohexenyl-CH₃ | | 49 |
| 9 | (CH₃)₃C | —CO— | cyclohexyl-H | | 210 (x ½ NDS) |
| 10 | (CH₃)₃C | —CO— | n-C₄H₉ | C₂H₅ | Oil |
| 11 | (CH₃)₃C | —CH(OH)— | cyclohexenyl | | 151 (Z-form) |
| 12 | (CH₃)₃C | —CH(OH)— | cyclohexenyl-CH₃ | | Oil |
| 13 | (CH₃)₃C | —CH(OC₃H₇—n)— | cyclohexyl-H | | Oil |

-continued $$R^1-X-C=CH-CH\begin{matrix}R^2\\R^3\end{matrix} \quad (I)$$

with triazole ring on C

| Example No. | R¹ | X | R² | R³ | Melting point (°C.) |
|---|---|---|---|---|---|
| 14 | $(CH_3)_3C$ | $-CH(O-CO-C_6H_5)-$ | phenyl (H) | | Oil |
| 15 | $(CH_3)_3C$ | $-CH(O-CO-CHCl_2)-$ | phenyl (H) | | Oil |
| 16 | $(CH_3)_3C$ | $-CH(O-CO-N(CH_3)(SCCl_3))-$ | phenyl (H) | | Oil |
| 17 | 2,4-Cl₂-C₆H₃ | $-CH(OH)-$ | phenyl (H) | | Oil |
| 18 | 2,4-Cl₂-C₆H₃ | $-CH(OH)-$ | $C_2H_5$ | $C_2H_5$ | Oil |
| 19 | 2,4-Cl₂-C₆H₃ | $-CH(OH)-$ | cyclohexenyl | | Oil |
| 20 | 2,4-Cl₂-C₆H₃ | $-CH(O-COCH_3)-$ | phenyl (H) | | Oil |
| 21 | $(CH_3)_3C$ | $-CCH_3(OH)-$ | phenyl (H) | | 101 |
| 22 | $(CH_3)_3C$ | $-CH(OH)-$ | phenyl (H) | | 154 (.HCl) (Z-form) |
| 23 | 2,4-Cl₂-C₆H₃ | $-CH(OH)-$ | $C_3H_7$ | $CH_3$ | Oil |

-continued

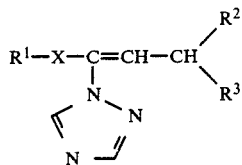
(I)

| Example No. | R¹ | X | R² | R³ | Melting point (°C.) |
|---|---|---|---|---|---|
| 24 | $(CH_3)_3C$ | —CH(OH)— | cyclohexyl | H | 110 (·$CuCl_2$) (Z-form) |
| 25 | 2,4-dichlorophenyl | —CH(O—CO—$NHCH_3$)— | cyclohexyl | H | 62 |
| 26 | 2,4-dichlorophenyl | —CH(OH)— | $C_2H_5$ | $CH_3$ | Oil |
| 27 | 2,4-dichlorophenyl | —CH(O—CO—phenyl)— | $C_3H_7$ | $CH_3$ | Oil |
| 28 | 2,4-dichlorophenyl | —CH(O—CO—$CH_3$)— | $C_3H_7$ | $CH_3$ | Oil |
| 29 | $(CH_3)_3C$ | —CH(O—$CH_2$—(2,4-dichlorophenyl))— | cyclohexyl | H | Oil (Z-form) |
| 30 | $ClCH_2$—$C(CH_3)_2$— | —CO— | cyclohexyl | H | 51 |
| 31 | $ClCH_2$—$C(CH_3)_2$— | —CO— | cyclohexenyl | | Oil |
| 32 | $ClCH_2$—$C(CH_3)_2$— | —CH(OH)— | cyclohexyl | H | Oil |
| 33 | 4-biphenylyl | —CH(OH)— | cyclohexyl | H | 156 |

-continued

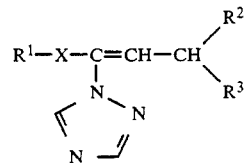
(I)

| Example No. | R¹ | X | R² | R³ | Melting point (°C.) |
|---|---|---|---|---|---|
| 34 | (CH₃)₃C | —CH(OH)— | cyclohexyl | H | 153 (.HNO₃) (Z-form) |
| 35 | 2,4-dichlorophenyl | —CH(OH)— | norbornenyl | | Oil |
| 36 | 4-chlorophenyl | —CH(OH)— | cyclohexyl | H | Oil |
| 37 | phenyl | —CH(OH)— | cyclohexyl | H | Oil |
| 38 | 4-fluorophenyl | —CH(OH)— | C₂H₅ | CH₃ | Oil |
| 39 | biphenyl | —CH(OH)— | C₂H₅ | CH₃ | Oil |
| 40 | biphenyl | —CH(OH)— | C₄H₉ | C₂H₅ | Oil |
| 41 | ClCH₂—C(CH₃)₂— | —CH(OH)— | cyclohexenyl | | Oil |
| 42 | (CH₃)₃C | —CH(OCH₃)— | cyclohexyl | H | 63 (Z-form) |
| 43 | 4-fluorophenyl | —CH(OH)— | C₄H₉ | C₂H₅ | Oil |
| 44 | FCH₂—C(CH₃)₂— | —CO— | C₄H₉ | C₂H₅ | Oil |
| 45 | (CH₃)₃C | —CH(OCH₃)— | cyclohexyl | H | 104 (E-form) |

-continued $$R^1-X-C=CH-CH\begin{matrix}R^2\\R^3\end{matrix}$$ (I)

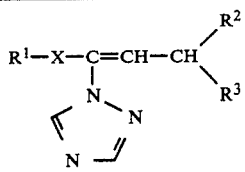

| Example No. | $R^1$ | X | $R^2$ | $R^3$ | Melting point (°C.) |
|---|---|---|---|---|---|
| 46 | $(CH_3)_3C$ | —CH(OH)— | cyclohexyl (H) | | 137 (.HNO$_3$) (E-form) |
| 47 | 4-Cl-biphenyl | —CH(OH)— | $CH_3$ | $CH_3$ | 187 |
| 48 | $ClCH_2$—$C(CH_3)_2$— | —CH(OH)— | $CH_3$ | $CH_3$ | Oil |
| 49 | $(CH_3)_3C$ | —CH(OH)— | cyclohexyl (H) | | 242 (.½ NDS) (E-form) |
| 50 | $(CH_3)_3C$ | —CH(OH)— | cyclohexyl (H) | | 168 (.CuCl$_2$) (E-form) |
| 51 | $(CH_3)_3C$ | —CO— | cyclohexyl (H) | | 137–140 (.CuCl$_2$) (E-form) |
| 52 | 4-Cl-biphenyl | —CH(OH)— | cyclohexyl (H) | | 157 |
| 53 | 4-Cl-biphenyl | —CH(OH)— | $C_4H_9$ | $C_2H_5$ | 118 |
| 54 | $FCH_2$—$C(CH_3)_2$— | —CO— | cyclohexenyl | | Oil |
| 55 | $FCH_2$—$C(CH_3)_2$— | —CO— | cyclohexyl (H) | | Oil |
| 56 | $FCH_2$—$C(CH_3)_2$— | —CH(OH)— | cyclohexyl (H) | | Oil |
| 57 | $FCH_2$—$C(CH_3)_2$— | —CH(OH)— | cyclohexenyl | | Oil |

-continued

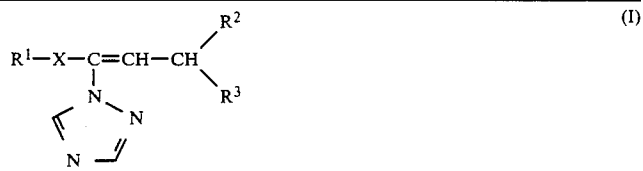

(I)

| Example No. | R¹ | X | R² | R³ | Melting point (°C.) |
|---|---|---|---|---|---|
| 58 | $FCH_2-C(CH_3)_2-$ | $-CO-$ | cyclohexyl with H | | Oil (Z-form) |
| 59 | $FCH_2-C(CH_3)_2-$ | $-CO-$ | cyclohexenyl | | Oil (Z-form) |
| 60 | $ClCH_2-C(CH_3)_2-$ | $-CO-$ | cyclohexyl with H | | 103 (E-form) |
| 61 | 4'-chloro-biphenyl | $-CH(OH)-$ | | | 144 |
| 62 | 4'-chloro-biphenyl | $-CH(OH)-$ | $C_2H_5$ | $C_2H_5$ | 148 |
| 63 | $FCH_2-C(CH_3)_2-$ | $-CH(OH)-$ | cyclohexenyl | | $n_D^{20}$: 1,5049 (Z-form) |
| 64 | $FCH_2-C(CH_3)_2-$ | $-CH(OH)-$ | cyclohexyl with H | | $n_D^{20}$: 1,4910 (Z-form) |
| 65 | $ClCH_2-C(CH_3)_2-$ | $-CH(OH)-$ | cyclohexyl with H | | $n_D^{20}$: 1,5050 (E-form) |

E- and Z-form: the two possible geometric isomer forms
NDS: 1,5-naphthalindisulfonic acid It will be understood that the specification and examples are illustrative, but not limitative of the present invention and that other embodiments within the spirit and scope of the invention will suggest themselves to those skilled in the art.

What is claimed is:

1. 1-vinyltriazole compounds of the formula

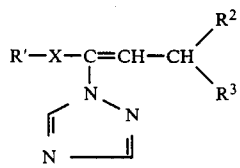

wherein
R¹ is optionally halogen substituted alkyl with 1 to 4 carbon atoms
R² and R³, together with the carbon atoms to which they are bonded, represent cycloalkenyl with 5 to 7 carbon atoms, or substituted cycloalkenyl wherein the substituent is alkyl with 1 to 4 carbon atoms; or cycloalkyl with 3 to 7 carbon atoms,
X is the group $-C(OR^4)R^5-$
R⁴ is hydrogen, alkyl with from 1 to 4 carbon atoms, benzyl or substituted benzyl wherein the substituent is selected from halogen, or is the acyl radical $-CO-R^{10}$, or the carbamoyl radical $-CO-NR^{11}R^{12}$, $R^5$ is hydrogen, alkyl with from 1 to 4 carbon atoms or benzyl, $R^{10}$ is alkyl with 1 to 4 carbon atoms, haloalkyl with 1 to 2 carbon atoms and 1 to 4 identical or different halogen atoms or phenyl, $R^{11}$ is hydrogen or alkyl with 1 to 4 carbon atoms, and $R^{12}$ is alkyl with 1 to 8 carbon atoms, haloalkyl with up to 4 carbon atoms and up to 5 identical or different halogen atoms, phenyl, or haloalkylmercapto with 1 to 2 carbon atoms and up to 5 halogen atoms, and acid addition salts and metal salt complexes thereof.

2. 1-Vinyltriazole compound as claimed in claim 1 wherein $R^2$ and $R^3$, together with the carbon atom to which they are bonded, represent cycloalkyl.

3. 1-Vinyltriazole compound as claimed in claim 1 wherein $R^4$ is hydrogen.

4. 1-Vinyltriazole compound as claimed in claim 1 wherein $R^4$ is alkyl of up to 4 carbon atoms.

5. 1-Vinyltriazole compound as claimed in claim 1 wherein $R^4$ is benzyl.

6. 1-vinyltriazole compound as claimed in claim 1 wherein $R^4$ is acyl of the formula —CO—$R^{10}$, wherein $R^{10}$ is alkyl with 1 to 4 carbon atoms, haloalkyl with 1 to 2 carbon atoms and 1 to 4 identical or different halogen atoms or phenyl.

7. 1-Vinyltriazole compound as claimed in claim 1 wherein $R^4$ is carbamoyl —CO—$NR^{11}R^{12}$, wherein $R^{11}$ is hydrogen or alkyl with 1 to 4 carbon atoms, and $R^{12}$ is alkyl with 1 to 8 carbon atoms, haloalkyl with up to 4 carbon atoms and up to 5 identical or different halogen atoms, phenyl; or haloalkylmercapto with 1 to 2 carbon atoms and up to 5 halogen atoms.

8. 1-Vinyltriazole compound as claimed in claim 1 in the form of an acid addition salt thereof.

9. 1-Vinyltriazole compound as claimed in claim 1 in the form of a metal salt complex thereof.

10. 1-Vinyltriazole compound as claimed in claim 1 designated 1-cyclohexyl-4,4-dimethyl-2-(1,2,4-triazol-1-yl)-pent-1-en-3-ol.

11. 1-Vinyltriazole compound as claimed in claim 1 designated 1-cyclohexyl-3-ethoxy-4,4-dimethyl-2-(1,2,4-triazol-1-yl)-pent-1-ene.

12. 1-Vinyltriazole compound as claimed in claim 1 designated 3-acetoxy-1-cyclohexyl-4,4-dimethyl-2-(1,2,4-triazol-1-yl)-pent-1-ene.

13. 1-Vinyltriazole compound as claimed in claim 1 designated 1-(methylcyclohex-3-en-yl)-4,4-dimethyl-2-(1,2,4-triazol-1-yl)-pent-1-en-3-ol.

14. 1-Vinyltriazole compound as claimed in claim 1 wherein said compound is selected from
1-cyclohexyl-3-ethoxy-4,4-dimethyl-2-(1,2,4-triazol-1-yl)-pent-1-en-3-ol
1-cyclohexyl-3-ethoxy-4,4-dimethyl-2-(1,2,4-triazol-1-yl)-pent-1-ene
3-acetoxy-1-cyclohexyl-4,4-dimethyl-2-(1,2,4-triazol-1-yl)-pent-1-ene, and
1-(methylcyclohex-3-en-yl)-4,4-dimethyl-2-(1,2,4-triazol-1-yl)-pent-1-en-3-ol.

15. Plant growth regulant composition comprising a compound as claimed in claim 1 in admixture with a solid or liquefied diluent or carrier containing a surface-active agent.

16. Plant growth regulant composition as claimed in claim 33 containing from 0.1 to 95% of the active compound, by weight.

17. Fungicidal composition comprising a compound as claimed in claim 1 in admixture with a solid or liquefied diluent or carrier containing a surface-active agent.

18. Fungicidal composition comprising a compound as claimed in claim 17 containing from 0.1 to 95% of the active compound, by weight.

19. Method for regulating plant growth, which method comprises applying to the plants or their habitat, an effective amount of a 1-vinyltriazole compound as claimed in claim 1.

20. Method as claimed in claim 19 wherein the active compound is applied to an area of agriculture in an amount of 0.01 to 50 kg per hectare.

21. Method as claimed in claim 19 wherein the active compound is applied to an area of agriculture in an amount of 0.05 to 10 kg per hectare.

22. Method as claimed in claim 19 wherein the compound is applied in a composition containing from 0.0001 to 1% of the active compound by weight.

23. Method as claimed in claim 19 wherein the composition used contains from 0.001 to 0.5% of the active compound by weight.

24. Method as claimed in claim 19 wherein the compound is applied to the soil in an amount of 0.0001 to 0.1% by weight.

25. Method as claimed in claim 19 wherein the compound is applied to the soil in an amount of 0.0001 to 0.2% by weight.

26. Method as claimed in claim 19 wherein the compound is applied to the seed in an amount of 0.001 to 50 grams per kg of seed.

27. Method as claimed in claim 19 wherein the compound is applied to the seed in an amount of 0.01 to 10 grams per kg of seed.

28. Method for combating fungi, which method comprises applying to the fungi, or to a habitat thereof, a 1-vinyltriazole compound as claimed in claim 1.

29. Method for combating fungi as claimed in claim 28 wherein the active compound is applied to an area of agriculture in an amount of 0.01 to 50 kg per hectare.

30. Method for combating fungi as claimed in claim 28 wherein the active compound is applied to an area of agriculture in an amount of 0.05 to 10 kg per hectare.

31. Method for combating fungi as claimed in claim 28 wherein the composition used contains from 0.0001 to 1% of the active compound by weight.

32. Method for combating fungi as claimed in claim 28 wherein the compound is applied in a composition containing from 0.001 to 0.5% of the active compound by weight.

33. Method for combating fungi as claimed in claim 28 wherein the compound is applied to the soil in an amount of 0.00001 to 0.1% by weight.

34. Method for combating fungi as clamed in claim 28 wherein the compound is applied to the soil in an amount of 0.0001 to 0.2% by weight.

35. Method for combating fungi as claimed in claim 28 wherein the compound is applied to the seed in an amount of 0.001 to 50 grams per kg of seed.

36. Method for combating fungi as claimed in claim 28 wherein the compound is applied to the seed in an amount of 0.01 to 10 grams per kg of seed.

* * * * *

UNITED STATES PATENT AND TRADEMARK OFFICE
CERTIFICATE OF CORRECTION

PATENT NO. : 4,486,218

DATED : December 4, 1984

INVENTOR(S) : Wolf Reiser, et al

It is certified that error appears in the above-identified patent and that said Letters Patent is hereby corrected as shown below:

Title Page, under "[22] Filed:" insert

--[30] Foreign Application Priority Data
Feb. 16, 1979 [DE] Fed. Rep. of Germany...2906061 and
Sep. 22, 1979 [DE] Fed. Rep. of Germany...2938422--

Signed and Sealed this

Twenty-seventh Day of March, 1990

Attest:

JEFFREY M. SAMUELS

*Attesting Officer*   *Acting Commissioner of Patents and Trademarks*